(12) United States Patent
Tominaga et al.

(10) Patent No.: US 8,987,505 B2
(45) Date of Patent: Mar. 24, 2015

(54) METHOD FOR PRODUCING LACTIC ACIDS FROM CARBOHYDRATE-CONTAINING RAW MATERIAL

(75) Inventors: Kenichi Tominaga, Ibaraki (JP); Atsushi Mori, Ibaraki (JP); Kazuhiko Satoh, Ibaraki (JP); Shigeru Shimada, Ibaraki (JP); Hideaki Tsuneki, Osaka (JP); Yoshiaki Hirano, Tokyo (JP)

(73) Assignees: Nippon Shokubai Co., Ltd, Osaka (JP); National Institute of Advanced Industrial Science and Technology, Tokyo (JP)

( * ) Notice: Subject to any disclaimer, the term of this patent is extended or adjusted under 35 U.S.C. 154(b) by 32 days.

(21) Appl. No.: 13/638,014

(22) PCT Filed: Mar. 31, 2011

(86) PCT No.: PCT/JP2011/058294
§ 371 (c)(1),
(2), (4) Date: Nov. 29, 2012

(87) PCT Pub. No.: WO2011/125882
PCT Pub. Date: Oct. 13, 2011

(65) Prior Publication Data
US 2013/0204036 A1    Aug. 8, 2013

(30) Foreign Application Priority Data

Mar. 31, 2010 (JP) .................. 2010-082174
Mar. 31, 2010 (JP) .................. 2010-082834
Oct. 29, 2010 (JP) .................. 2010-244406
Oct. 29, 2010 (JP) .................. 2010-244486
Oct. 29, 2010 (JP) .................. 2010-244542

(51) Int. Cl.
*C07C 69/68* (2006.01)
*B01J 31/12* (2006.01)
*C07C 51/16* (2006.01)
*C07C 67/03* (2006.01)
*C07C 67/00* (2006.01)
*C07C 51/00* (2006.01)

(52) U.S. Cl.
CPC .................. *C07C 51/16* (2013.01); *C07C 67/03* (2013.01); *C07C 67/00* (2013.01); *C07C 51/00* (2013.01)
USPC .......................................... 560/179; 502/102

(58) Field of Classification Search
USPC .......................................... 560/179; 502/102
See application file for complete search history.

(56) References Cited

U.S. PATENT DOCUMENTS 5,932,511 A * 8/1999 Harmer et al. ................. 502/159

FOREIGN PATENT DOCUMENTS

| JP | 56-030943 | * 3/1981 |
| JP | 04-356436 | 12/1992 |
| JP | 2004-359660 | * 12/2004 |
| JP | 2008-120796 | 5/2008 |
| WO | WO 2008/056330 | 5/2008 |
| WO | WO2008/109877 | 9/2008 |

OTHER PUBLICATIONS

Mori, Atsushi, et al., "Suzu Shokubai o Mochiita Torui kara no Shokubaiteki Nyusan Gosei", Shokubai Toronkai Toronkai A Yokoshu, Sep. 15, 2010, vol. 106, p. 160.

Holm, Martin Spangsberg, et al., "Conversion of Sugars to Lactic Acid Derivatives Using Heterogeneous Zeotype Catalysts", Science, Apr. 30, 2010, vol. 328, pp. 602-605.

* cited by examiner

*Primary Examiner* — Kamal Saeed
*Assistant Examiner* — Janet L Coppins
(74) *Attorney, Agent, or Firm* — McCarter & English

(57) ABSTRACT

An alternative method for efficiently producing lactic acids from a carbohydrate-containing raw material such as cellulose is provided. The method for producing lactic acid and/or lactic acid ester comprises performing heat treatment on a carbohydrate-containing raw material in a solvent containing a catalyst, wherein the catalyst is at least one type of compound selected from the group consisting of a tin compound, an indium compound, and a rhenium compound, and the solvent contains water and/or alcohol.

9 Claims, 2 Drawing Sheets

METHOD FOR PRODUCING LACTIC ACIDS FROM CARBOHYDRATE-CONTAINING RAW MATERIAL

RELATED APPLICATIONS

This application is a national stage application filed under 35 USC §371 of PCT/JP2011/058294, filed Mar. 31, 2011, which claims the benefit of Japanese Patent Application Nos. 2010-082834 and 2010-082174, filed Mar. 31, 2010, and Japanese Patent Application Nos. 2010-244406, 2010-244486 and 2010-244542, filed Oct. 29, 2010, each of which are incorporated herein, in entirety, by reference.

TECHNICAL FIELD

The present invention relates to a method for producing lactic acids from a carbohydrate-containing raw material using as a catalyst at least one type of compound selected from the group consisting of a tin compound, an indium compound, and a rhenium compound.

BACKGROUND ART

Methods for producing lactic acid that are currently performed industrially are based on lactic fermentation of saccharides (see Patent Literature 1). However, such methods are problematic in that cellulose should be subjected to a saccharification step using acid, an enzyme, or the like so that cellulose can be used as a raw material for lactic fermentation. Also, in general, lactic acid production methods based on fermentation are problematic in that the reaction rates are low, huge fermentation tanks are required, the concentrations of the thus generated lactic acid are low, and the resulting energy consumption for purification is high. Furthermore, the solution pH decreases as lactic fermentation proceeds, resulting in decreased lactic acid bacteria fermentation efficiency. Accordingly, lactic fermentation is performed while neutralizing the solution with a base. Therefore, the product generated by the lactic fermentation methods is lactate, lactate is treated with acid to liberate lactic acid from lactate, and then the treatment of a neutralization salt resulting therefrom also poses significant problems in terms of processes.

As a lactic acid production method not based on any biological technique, a chemical method is known that involves treating carbohydrates hydrothermally in the presence of an alkali. For example, when a saccharide (see Non-Patent Literature 1 and Non-Patent Literature 2), cellulose (see Patent Literature 2 and Non Patent Literature 3), or organic waste (see Non-Patent Literature 4) is treated by the method, some carbohydrates that have been degraded under high-temperature and high-pressure reaction conditions are isomerized to generate lactic acid. However, the method is problematic in that lactic acid reacts with the alkali added as a catalyst to result in lactate, some inorganic acids must be added to the reaction solution to make the solution acidic for separation of lactic acid as acid, and thus alkali and inorganic acid are stoichiometrically consumed.

As a chemical method for producing lactic acid without using an alkali, a method has been reported that involves reacting starch, oligosaccharide, or monosaccharide with alcohol using a metal halide as a catalyst, so as to convert it into lactic acid ester (see Patent Literature 3). However, as a result of examination by the present inventors, a cellulose-based raw material could not be degraded by this method at less than 200° C., and generation of lactic acid or lactic acid ester could not be confirmed.

An example has also been reported wherein a cellulose-based raw material is directly converted to lactic acid by a chemical reaction without using an alkali. However, the method requires very high-temperature and high-pressure (temperature of 350° C. or higher and less than 400° C., and pressure of 20 MPa or more to 35 MPa) reaction conditions, and thus energy consumption is high and the yield of lactic acid is insufficient (see Patent Literature 4).

As other reports concerning lactic acid production from a cellulose-based raw material within a single step, an example of using a group III metal salt as a catalyst (see Patent Literature 5 and Patent Literature 6) and an example of using a rare-earth metal oxide as a catalyst have been reported (see Patent Literature 7). These methods exhibit high lactic acid yields only under conditions of a relatively low concentration of a raw material. A production method that exhibits a good lactic acid yield with a higher concentration of a raw material is desired from a practical standpoint.

PRIOR ART LITERATURE

Patent Literature

[Patent Literature 1] JP Patent Publication (Kokai) No. 6-311886 A (1994)
[Patent Literature 2] JP Patent Publication (Kokai) No. 2005-232116 A
[Patent Literature 3] JP Patent Publication (Kokai) No. 2004-359660 A
[Patent Literature 4] JP Patent Publication (Kokai) No. 2004-323403 A
[Patent Literature 5] JP Patent Publication (Kokai) No. 2008-120796 A
[Patent Literature 6] JP Patent Publication (Kokai) No. 2009-263242 A
[Patent Literature 7] JP Patent Publication (Kokai) No. 2009-263241A

Non Patent Literature

[Non Patent Literature 1] Byung Y. Y. and Montgomery R., Carbohydrate Research, Vol. 280 (1996) p. 27-45
[Non Patent Literature 2] Byung Y. Y. and Montgomery R., Carbohydrate Research, Vol. 280 (1996) p. 47-57
[Non Patent Literature 3] Niemelae K. and Sjoestroem E., Biomass, 11 (1986) p. 215-221
[Non Patent Literature 4] Armando T. Q. et al., Journal of Hazardous Materials, B93 (2002)

SUMMARY OF INVENTION

Technical Problem

An object of the present invention is to provide an alternative method for efficiently producing lactic acids from a carbohydrate-containing raw material.

Solution to Problem

As a result of intensive studies to achieve the above object, the present inventors have found that lactic acids (lactic acid and/or lactic acid ester) can be efficiently produced from a carbohydrate-containing raw material using as a catalyst at least one type of compound selected from the group consisting of a tin compound, an indium compound, and a rhenium compound, even when a small amount of the catalyst is used. Also, the present inventors have found that lactic acids (lactic acid and/or lactic acid ester) can be efficiently produced from a carbohydrate-containing raw material using at least one type of compound selected from the group consisting of a tin compound, an indium compound, and a rhenium compound and at least one type of compound selected from the group consisting of a first transition series metal compound, a lithium compound, a magnesium compound, an alkali metal salt, an alkaline earth metal salt, a quaternary ammonium salt, and a quaternary phosphonium salt, in combination as a catalyst. They have completed the present invention based on these findings.

Specifically, the present invention encompasses the following [1] to [9].

[1] A method for producing lactic acid and/or lactic acid ester by heat treatment on a carbohydrate-containing raw material in a solvent containing a catalyst, wherein:
the catalyst is at least one type of compound selected from the group consisting of a tin compound, an indium compound, and a rhenium compound; and
the solvent contains water and/or alcohol.

[2] The method for producing lactic acid/lactic acid ester of [1], wherein the solvent further contains at least one type of compound selected from the group consisting of a first transition series metal compound, a lithium compound, a magnesium compound, an alkali metal salt, an alkaline earth metal salt, a quaternary ammonium salt, and a quaternary phosphonium salt.

[3] The method for producing lactic acid/lactic acid ester of [1] or [2], wherein at least one type of compound selected from the group consisting of a tin compound, an indium compound, and a rhenium compound and at least one type of compound selected from the group consisting of a first transition series metal compound, a lithium compound, a magnesium compound, an alkali metal salt, an alkaline earth metal salt, a quaternary ammonium salt, and a quaternary phosphonium salt form an ate complex.

[4] The method for producing lactic acid/lactic acid ester of any one of [1] to [3], wherein the tin compound is selected from the group consisting of tin or organic tin perfluoroalkylsulfonate and a tin or organic tin halide.

[5] The method for producing lactic acid/lactic acid ester of any one of [1] to [4], wherein the indium compound is selected from the group consisting of a halide salt, carboxylate, indium alkoxide, and indium acetylacetate.

[6] The method for producing lactic acid/lactic acid ester of any one of [1] to [5], wherein the rhenium compound is a compound containing a halide or a carbonyl ligand.

[7] The method for producing lactic acid/lactic acid ester of any one of [1] to [6], wherein the solvent further contains a phenolic compound.

[8] The method for producing lactic acid/lactic acid ester of any one of [1] to [7], wherein heat treatment is performed at 100° C. to 300° C.

[9] The method for producing lactic acid/lactic acid ester of any one of [1] to [8], wherein the carbohydrate-containing raw material is at least one type selected from the group of cellulose, soluble polysaccharides, and monosaccharides.

Furthermore, the present invention encompasses the following (1) to (5).

(1) A method for producing lactic acid and/or lactic acid ester, comprising performing heat treatment on a carbohydrate-containing raw material in a water- and/or alcohol-containing solvent containing at least one type of tin or organic tin perfluoroalkylsulfonate.

(2) The method of (1), wherein the water- and/or alcohol-containing solvent further contains at least one type selected from the group consisting of a tin or organic tin halide, an indium compound, a rhenium compound, a magnesium compound, and a first transition series metal compound.

(3) The method of (1) or (2), wherein perfluoroalkylsulfonate is trifluoromethanesulfonate.

(4) The method of any one of (1) to (3), wherein the carbohydrate-containing raw material contains cellulose.

(5) The method of any one of (1) to (4), wherein the water- and/or alcohol-containing solvent further contains a phenolic compound.

Furthermore, the present invention encompasses the following <1> to <6>.

<1> A method for producing lactic acids, comprising performing heat treatment on a carbohydrate-containing raw material in a solvent containing water and/or alcohol, wherein the solvent contains as a catalyst at least one type of tin-containing compound selected from the group consisting of a tin or organic tin halide and tin or organic tin perfluoroalkylsulfonate, and as a promoter at least one type of compound selected from the group consisting of a lithium halide, a magnesium halide, a first transition series metal halide, and a quaternary ammonium salt.

<2> The method of <1>, wherein the tin or organic tin halide to be used as a catalyst is chloride.

<3> The method of <1> or <2>, wherein perfluoroalkylsulfonate to be used as a catalyst is trifluoromethanesulfonate.

<4> The method of any one of <1> to <3>, wherein the lithium halide, the magnesium halide, or the first transition series metal halide to be used as a promoter is chloride.

<5> The method of any one of <1> to <3>, wherein the quaternary ammonium salt to be used as a promoter is halide.

<6> The method of any one of <1> to <5>, wherein the heat treatment is performed by heating at 100° C. to 300° C.

Furthermore, the present invention encompasses the following [1] to [3].

[1] A method for producing lactic acid and/or lactic acid ester, comprising performing heat treatment on a carbohydrate-containing raw material in a water- and/or alcohol-containing solvent containing at least one type selected from the group consisting of indium alkoxide and indium acetylacetonate.

[2] The method of [1], wherein the water- and/or alcohol-containing solvent further contains a phenolic compound.

[3] The method of [1] or [2], wherein the heat treatment is performed by heating at 100° C. to 300° C.

Furthermore, the present invention encompasses the following {1} to {6}.

{1} A method for producing lactic acids, comprising performing heat treatment on a carbohydrate-containing raw material in a water- and/or alcohol-containing solvent containing at least one type of rhenium compound.

{2} The method of {1}, wherein at least one type of rhenium compound contains a carbonyl ligand.

{3} The method of {1} or {2}, wherein the water- and/or alcohol-containing solvent further contains at least one type of compound of a metal other than rhenium.

{4} The method of {3}, wherein at least one type of compound of a metal other than rhenium is selected from the group consisting of a magnesium compound and a first transition series metal compound.

{5} The method of {3} or {4}, wherein the rhenium compound and the compound of a metal other than rhenium generate a metal compound containing at least two types of metal including rhenium and a metal other than rhenium.

{6} The method of any one of {1} to {5}, wherein the heat treatment is performed by heating at 100° C. to 300° C.

Furthermore, the present invention encompasses the following <<1>> to <<9>>.

<<1>> A method for producing lactic acids, comprising performing heat treatment on a carbohydrate-containing raw material in a solvent containing water and/or alcohol using as catalysts, at least one type of metal compound selected from the group consisting of an indium compound, a gallium compound, an aluminium compound, a tin compound, and a rhenium compound, and at least one type of salt selected from the group consisting of an alkali metal salt, an alkaline earth metal salt, a first transition series metal salt, a quaternary ammonium salt, and a quaternary phosphonium salt.

<<2>> The method for producing lactic acids of <<1>>, wherein at least one type of metal compound selected from the group consisting of an indium compound, a gallium compound, an aluminium compound, a tin compound, and a rhenium compound and at least one type of salt selected from the group consisting of an alkali metal salt, an alkaline earth metal salt, a first transition series metal salt, a quaternary ammonium salt, and a quaternary phosphonium salt form an ate complex.

<<3>> The method for producing lactic acids of <<1>> or <<2>>, wherein at least one type of metal compound selected from the group consisting of an indium compound, a gallium compound, an aluminium compound, a tin compound, and a rhenium compound is selected from the group consisting of a halide salt and carboxylate.

<<4>> The method for producing lactic acids of <<3>>, wherein at least one type of metal compound selected from the group consisting of an indium compound, a gallium compound, an aluminium compound, a tin compound, and a rhenium compound is a chloride salt.

<<5>> The method for producing lactic acids of any one of <<1>> to <<4>>, wherein at least one type of salt selected from the group consisting of an alkali metal salt, an alkaline earth metal salt, a first transition series metal salt, a quaternary ammonium salt, and a quaternary phosphonium salt is selected from the group consisting of a halide salt, carboxylate, and borate.

<<6>> The method for producing lactic acids of any one of <<1>> to <<5>>, comprising using as a catalyst at least one type of tin or organic tin perfluoroalkylsulfonate.

<<7>> The method for producing lactic acids of <<6>>, wherein the perfluoroalkylsulfonate is trifluoromethanesulfonate.

<<8>> The method for producing lactic acids of <<6>> or <<7>>, wherein the carbohydrate-containing raw material contains cellulose.

<<9>> The method for producing lactic acids of any one of <<1>> to <<8>>, comprising performing heat treatment at 100° C. to 300° C.

This description includes part or all of the contents as disclosed in the description and/or drawings of Japanese Patent Application Nos. 2010-082834, 2010-244542, 2010-082174, 2010-244406, and 2010-244486 which are priority documents of the present application.

Advantageous Effects of Invention

According to the method of the present invention, lactic acids can be efficiently produced from a carbohydrate-containing raw material such as cellulose using a small amount of a catalyst.

DESCRIPTION OF EMBODIMENTS

Figure 1:
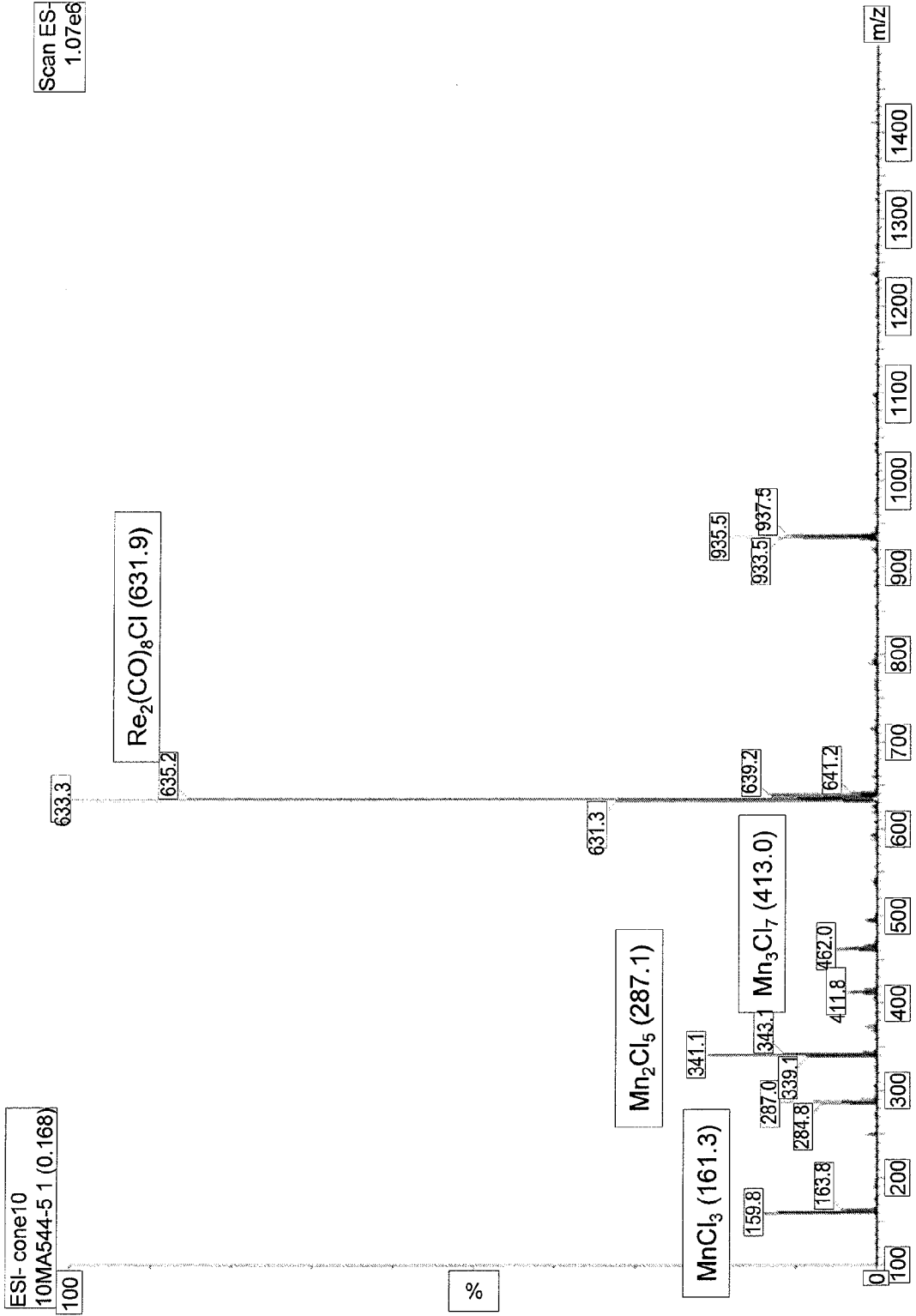
FIG. 1 shows the results of ESI/MS measurement for ate complexes generated by rhenium carbonyl and manganese chloride tetrahydrate.

According to the present invention, a reaction product containing lactic acid and/or lactic acid ester can be obtained by performing heat treatment on a carbohydrate-containing raw material in a water- and/or alcohol-containing solvent containing at least one type of compound selected from the group consisting of a tin compound, an indium compound, and a rhenium compound functioning as a catalyst.

Through the use of the method of the present invention, lactic acid and/or lactic acid ester can be conveniently produced with high efficiency from a carbohydrate in a carbohydrate-containing raw material, such as a polysaccharide (e.g., cellulose, starch, oligosaccharide, or disaccharide) or a monosaccharide (e.g., glucose or fructose), even when a small amount of a catalyst is used.

A reaction for generation of lactic acid or lactic acid ester from a carbohydrate-containing raw material proceeds as follows, for example, when cellulose is used as a starting material.

[Chemical formula 1]

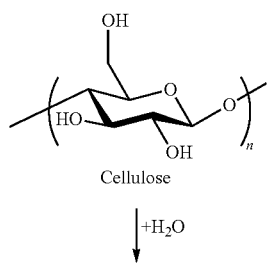

Cellulose $\downarrow$ +H$_2$O

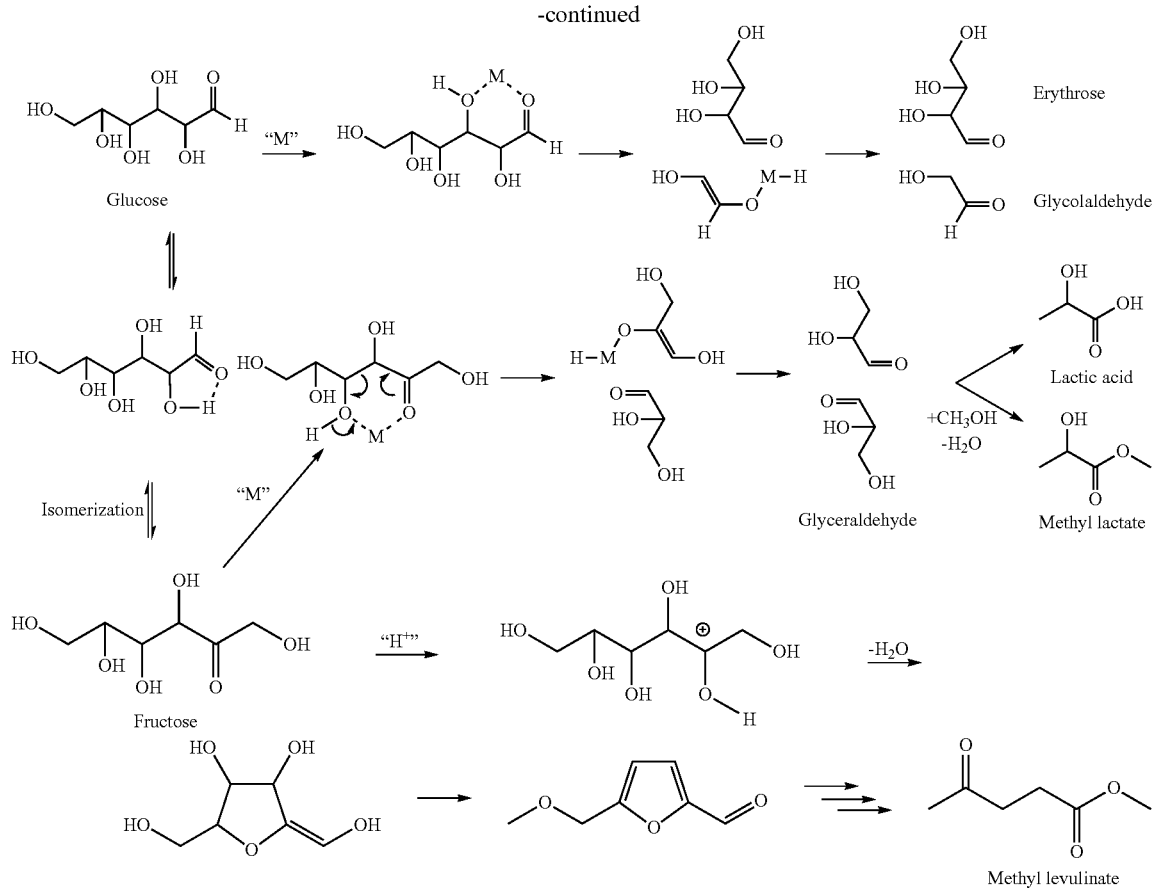

Cellulose is solvolysed under high temperature and high pressure in alcohol or water, so as to generate saccharides. Under the reaction conditions, the thus generated saccharides are further degraded to be converted to a low-molecular-weight compound, or instead, polymerize to form a carbonaceous high-molecular-weight compound. Examples of the degradation reaction include dehydration and retro-aldolization. 5-methoxymethylfurfural is generated through dehydration, and glycolaldehyde (diose), dihydroxyacetone or glyceraldehyde (triose), and erythritol (tetrose) are generated through retro-aldolization. Triose among these examples can be converted to lactic acid through isomerization. Furthermore, lactic acid is converted to lactic acid ester through dehydration and condensation reactions with alcohol.

A carbohydrate-containing raw material that can be used as a raw material for the method of the present invention may be any raw material containing carbohydrates. Such a carbohydrate-containing raw material may be any carbohydrate such as a monosaccharide, an oligosaccharide (prepared by the binding of 2 to 9 monosaccharides), or a polysaccharide (prepared by the binding of 10 or more monosaccharides), or an organism-derived material containing the same, but the examples are not limited thereto. As polysaccharides, cellulose or starch, oligosaccharides, or disaccharides are preferred, but the examples are not limited thereto. As monosaccharides, glucose and fructose are preferred, but the examples are not limited thereto. Carbohydrate-containing raw materials may be, for example, carbohydrates including hexose such as cellulose, holocellulose, cellobiose, starch (e.g., soluble starch), maltose, glucose, mannose, fructose, galactose, and glucose, hemicellulose-based substances including pentose such as hemicellulose, xylose, and arabinose, or raw materials containing at least one of them, such as lignocellulose-based raw materials. Carbohydrate-containing raw materials may also be biomass materials containing the above-mentioned carbohydrates (e.g., cellulose), for example, but the examples thereof are not particularly limited thereto. Examples of carbohydrate-containing raw materials include lignocellulose-based biomass materials including waste paper, remaining materials from lumber sawing, agricultural waste (e.g., straw, corn stober, corn cob, and ear of corn), and food waste including saccharides such as starch and glucose. A carbohydrate-containing raw material to be used in the method of the present invention preferably contains water in addition to carbohydrates such as cellulose.

In the present invention, examples of "tin compound" include, but are not limited to, tin or organic tin perfluoroalkylsulfonate, a tin or organic tin halide, an acetylacetone compound, an alkoxide compound, a carboxylate compound, a phosphate compound, a sulfate compound, and a nitrate compound. Preferably, such a tin compound is at least one type of compound selected from the group consisting of tin or organic tin perfluoroalkylsulfonate and a tin or organic tin halide. In the present invention, the term "organic tin" refers to tin (Sn) in which one or more organic substituents (hydrocarbon groups) are bound. Examples of a substituent binding to a tin atom of organic tin that can be used in the present invention include, but are not particularly limited to, a n-butyl group, a t-butyl group, a n-hexyl group, and a n-octyl group. Tin or organic tin perfluoroalkylsulfonate may be a tin (II) salt or a tin (IV) salt. Examples of "perfluoroalkylsulfonate" include, but are not particularly limited to, trifluoromethane sulfonate, pentafluoromethane sulfonate, heptafluoropropane sulfonate, and nonafluorobutane sulfonate. In the present invention, a more preferable example of perfluoroalkylsulfonate is trifluoromethane sulfonate (trivial name: triflate). As tin perfluoroalkylsulfonate, for example, tin (II) trifluoromethanesulfonate ($Sn(OTf)_2$) (Tf denotes a trifluoromethylsulfonyl group $CF_3SO_2$—. The same applies to the following) can be particularly preferably used. As organic tin perfluoroalkylsulfonate, for example, dibutyltin (II) trifluoromethanesulfonate can be particularly preferably used. Examples of such a "tin or organic tin halide" include tin or organic tin fluoride, chloride, bromide, and iodide. Examples of such a tin or organic tin halide include, but are not limited to, tin (II) chloride and di-n-butyltin (II) chloride.

Examples of an indium compound include indium halides (fluoride, chloride, bromide, and iodide), an acetylacetone compound, an alkoxide compound, a carboxylate compound, a phosphate compound, a sulfate compound, and a nitrate compound. A specific example thereof is, but is not limited to, indium bromide ($InBr_3$).

Examples of a rhenium compound include rhenium halides (fluoride, chloride, bromide, and iodide), an acetylacetone compound, an alkoxide compound, a carboxylate compound, a phosphate compound, a sulfate compound, a nitrate compound, and a compound containing a carbonyl ligand. A specific example of such a rhenium compound is, but is not limited to, rhenium carbonyl ($Re_2(CO)_{10}$).

In one reaction system, one type of compound selected from the group consisting of a tin compound, an indium compound, and a rhenium compound may be used and two or more types thereof may be used in combination.

A solvent containing water and/or alcohol to be used in the method of the present invention is a solution containing water or alcohol or a solution containing the two. The solvent may be water or alcohol alone, a mixture of water and alcohol, or a solution prepared by mixing them with other components such as other organic solvents. As water, distilled water, ion exchanged water, industrial water, or the like can be used. Alcohol to be used herein is not particularly limited, and is preferably aliphatic alcohol having a carbon number ranging from 1 to 8. Examples thereof include methanol, ethanol, propanol, isopropanol, 1-butanol, 2-butanol, and ethylene glycol. Hydrous alcohol can also be preferably used as a solvent in the present invention. One, two or more types of alcohol may be contained in a solvent. Also, in the method of the present invention, water is used as a solvent when lactic acid is produced, and a solvent containing alcohol is used when lactic acid ester is produced.

The amount of a solvent containing water and/or alcohol to be used with respect to that of a carbohydrate-containing raw material can be appropriately selected by a person skilled in the art, and is not particularly limited. The weight ratio of a carbohydrate-containing raw material to the amount of such a solvent generally ranges from 1:1 to 1:1000 (=raw material: solvent) and preferably ranges from 1:5 to 1:100.

The total amount of a compound(s) (to be used herein) selected from the group consisting of a tin compound, an indium compound, and a rhenium compound to be contained in a solvent containing water and/or alcohol is not limited. A compound(s) can be used in an amount corresponding to 0.001 mol to 1.0 mol, and preferably 0.005 mol to 0.1 mol, such as 0.01 mol to 0.05 mol (in terms of mass ratio) with respect to 1 mol of glucose residue in the carbohydrate-containing raw material. When such a compound(s) is used in an excessively low amount, degradation of polysaccharides such as cellulose proceeds with difficulty, and when the same is used in an excessively high amount, the yield of lactic acid or the yield of lactic acid ester decreases because of side reactions. Such amounts are not preferred.

In the method of the present invention, in addition to at least one type of compound selected from the group consisting of a tin compound, an indium compound, and a rhenium compound, at least one type of compound selected from the group consisting of a first transition series metal compound, a lithium compound, a magnesium compound, an alkali metal salt, an alkaline earth metal salt, a quaternary ammonium salt, and a quaternary phosphonium salt can also be used as another catalyst in combination.

Through the combined use of at least one type of compound selected from the group consisting of a first transition series metal compound, a lithium compound, a magnesium compound, an alkali metal salt, an alkaline earth metal salt, a quaternary ammonium salt, and a quaternary phosphonium salt as another catalyst, in addition to at least one type of compound selected from the group consisting of a tin compound, an indium compound, and a rhenium compound, lactic acid and/or lactic acid ester can be efficiently produced from polysaccharides and monosaccharides.

Examples of first transition series metal compounds include halides (fluoride, chloride, bromide, and iodide) of the first transition series metals (that is, scandium, titanium, vanadium, chromium, manganese, iron, cobalt, nickel, copper, and zinc), an acetylacetone compound, an alkoxide compound, a carboxylate compound, a phosphate compound, a sulfate compound, a nitrate compound, a boric acid compound, and a phenol compound. Examples thereof preferably include, but are not limited to, halides (particularly, chloride), a carboxylate compound, a boric acid compound, and a phenol compound. Specific examples thereof include manganese chloride tetrahydrate, manganese chloride tetrahydrate, cobalt chloride hexahydrate, cobalt chloride hexahydrate, nickel chloride tetrahydrate, and iron (II) chloride hexahydrate.

Examples of a lithium compound include halides (fluoride, chloride, bromide, and iodide), an acetylacetone compound, an alkoxide compound, a carboxylate compound, a phosphate compound, a sulfate compound, a nitrate compound, a boric acid compound, and a phenol compound. Preferably examples thereof include, but are not limited to, halides (particularly, chloride), a carboxylate compound, a boric acid compound, and a phenol compound. A specific example thereof is a lithium chloride.

Examples of a magnesium compound include magnesium halides (fluoride, chloride, bromide, and iodide), an acetylacetone compound, an alkoxide compound, a carboxylate compound, a phosphate compound, a sulfate compound, a nitrate compound, a boric acid compound, and a phenol compound. Preferably examples thereof include, but are not limited to, halides (particularly, chloride), a carboxylate compound, a boric acid compound, and a phenol compound. Specific examples thereof include magnesium chloride tetrahydrate ($MgCl_2.4H_2O$) and magnesium chloride hexahydrate ($MgCl_2.6H_2O$).

Examples of an alkali metal salt, an alkaline earth metal salt, and a quaternary phosphonium salt include a halide salt, carboxylate, borate, and a phenyl compound. Specific examples thereof include, but are not limited to, bis(triphenylphosphine)iminium chloride ([PPN]Cl), bis(triphenylphosphine)iminium bromide ([PPN]Br), bis(triphenylphosphine) iminium iodine ([PPN]I), bis (triphenylphosphine) iminium carboxylic acid ([PPN] OOCH), tetraethylammonium chloride ($Et_4NCl$), triethylamine hydrochloride ($Et_3NHCl$), trioctylmethylammonium chloride ($Oct_3NMeCl$), triethyl(2-methoxyethoxymethyl)ammonium chloride ($MeOCH_2CH_2OCH_2NEt_3Cl$), 1-butyl-3-methylimidazoliumchloride ([bmim]Cl), 1-butyl-3-methylimidazoliumacetate ([bmim]OAc), 1-butyl-2,3-dimethylimidazolium chloride ([bdmim]Cl), 1-butyl-3-methylimidazoliumtetrafluoroborate ([bmim]$BF_4$), tetraphenyl phosphonium chloride ($Ph_4PCl$), lithium chloride, sodium picolinate, and sodium(trihydroxy)phenylborate.

Examples of a quaternary ammonium salt include, but are not particularly limited to, quaternary ammonium salt halides (fluoride, chloride, bromide, and iodide), a carboxylic acid compound, a boric acid compound, and a phenol compound. For example, bis(triphenylphosphine)iminium chloride, tetrabutylammoniumbromide, trioctylmethylammoniumchloride, and the like can be particularly preferably used.

A first transition series metal compound can be used in an amount corresponding to 0 mol to 1.0 mol with respect to 1.0 mol of at least one type of compound selected from the group consisting of a tin compound, an indium compound, and a rhenium compound. The first transition series metal compound is preferably used in an amount equivalent to or lower than that of at least one type of compound selected from the group consisting of a tin compound, an indium compound, and a rhenium compound. The first transition series metal compound is further preferably used in an amount ranging from 0.01 mol to 0.9 mol (e.g., 0.2 mol to 0.8 mol) with respect to 1.0 mol of at least one type of compound selected from the group consisting of a tin compound, an indium compound, and a rhenium compound.

A lithium compound is used in an amount ranging from 0.1 mol to 10.0 mol with respect to 1.0 mol of at least one type of compound selected from the group consisting of a tin compound, an indium compound, and a rhenium compound. Preferably, a lithium compound is used in an amount equivalent to or higher than that of at least one type of compound selected from the group consisting of a tin compound, an indium compound, and a rhenium compound. Further preferably, a lithium compound is used in an amount ranging from 1.0 mol to 4.0 mol.

A magnesium compound can be used in an amount corresponding to 0 mol to 1.0 mol with respect to 1.0 mol of that of at least one type of compound selected from the group consisting of a tin compound, an indium compound, and a rhenium compound. A magnesium compound is preferably used in the same amount as or lower than that of at least one type of compound selected from the group consisting of a tin compound, an indium compound, and a rhenium compound. A magnesium compound is further preferably used in an amount ranging from 0.01 mol to 0.9 mol (e.g., 0.2 mol to 0.8 mol) with respect to 1.0 mol of that of at least one type of compound selected from the group consisting of a tin compound, an indium compound, and a rhenium compound.

An alkali metal salt, an alkaline earth metal salt, or a quaternary phosphonium salt can be used in an amount corresponding to 0 mol to 100 mol with respect to 1.0 mol of that of at least one type of compound selected from the group consisting of a tin compound, an indium compound, and a rhenium compound. An alkali metal salt, alkaline earth metal salt, or quaternary phosphonium salt can be further preferably used in an amount ranging from 0.01 mol to 10.0 mol (e.g., 0.1 mol to 1.0 mol) with respect to 1.0 mol of that of at least one type of compound selected from the group consisting of a tin compound, an indium compound, and a rhenium compound.

A quaternary ammonium salt is used in an amount ranging from 0.1 mol to 10.0 mol with respect to 1.0 mol of that of at least one type of compound selected from the group consisting of a tin compound, an indium compound, and a rhenium compound. A quaternary ammonium salt is preferably used in an amount equivalent to or higher than that of at least one type of compound selected from the group consisting of a tin compound, an indium compound, and a rhenium compound. A quaternary ammonium salt is further preferably used in an amount ranging from 1.0 mol to 4.0 mol.

In addition, in the Description, at least one type of compound selected from the group consisting of a lithium halide, a magnesium halide, a first transition series metal halide, and a quaternary ammonium salt may particularly be referred to as "promoter." Here, the term "promoter" refers to, in the presence of a tin compound, an indium compound and/or a rhenium compound, a compound that acts in concert with the tin compound, the indium compound and/or the rhenium compound, so as to accelerate and/or enhance degradation reaction of polysaccharides such as cellulose and sugar degradation•isomerization reaction. Such a promoter itself may be capable of or incapable of independently (that is, in the absence of tin or organic tin perfluoroalkylsulfonate or a tin compound, an indium compound, or a rhenium compound) catalyzing the degradation reaction of cellulose and sugar degradation•isomerization reaction. Therefore, examples of such a "promoter" are not limited to a lithium halide, a magnesium halide, a first transition series metal halide, and a quaternary ammonium salt, but can include various compounds described above.

In the method of the present invention, when at least one type of compound selected from the group consisting of a tin compound, an indium compound, and a rhenium compound is used in combination with at least one type of compound selected from the group consisting of a first transition series metal compound, a lithium compound, a magnesium compound, an alkali metal salt, an alkaline earth metal salt, a quaternary ammonium salt, and a quaternary phosphonium salt, these compounds may bind to each other in a reaction solution so as to form one or more types of ate complex. The term "ate complex" refers to a complex-type metal acid salt generated by coordination of anionic species (supplied from a compound such as a first transition series metal compound, a lithium compound, a magnesium compound, an alkali metal salt, an alkaline earth metal salt, a quaternary ammonium salt, or a quaternary phosphonium salt) to a compound having Lewis acidity, such as a tin compound, an indium compound, or a rhenium compound.

Through the use of an ate complex as a catalyst, retro-aldol reaction of sugar can be selectively caused to proceed while suppressing cyclization of sugar as described below. Therefore, an isomerization reaction to result in lactic acids can be more efficiently conducted from a carbohydrate-containing raw material.

[Chemical formula 2]

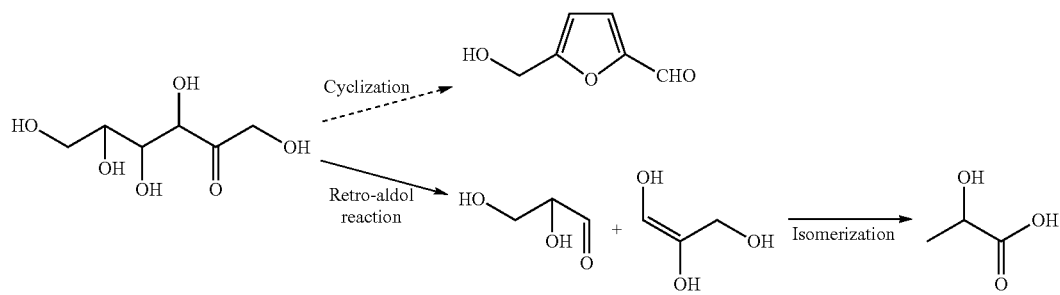

In the method of the present invention, in addition to at least one type of compound selected from the group consisting of a tin compound, an indium compound, and a rhenium compound and at least one type of compound selected from the group consisting of a first transition series metal compound, a lithium compound, a magnesium compound, an alkali metal salt, an alkaline earth metal salt, a quaternary ammonium salt, and a quaternary phosphonium salt, a phenolic compound can further be added to a solvent and then used. Examples of a phenolic compound include, but are not particularly limited to catechol, 3-fluorocatechol, 2,2'-biphenol, and 3-quinolinol. The amount of a phenolic compound to be used herein can be appropriately regulated by a person skilled in the art, preferably ranging from 0.1 mol to 10.0 mol and further preferably ranging from 1.0 mol to 4.0 mol with respect to 1.0 mol of that of the above compound.

In the method of the present invention, when a compound comprising at least one type selected from the group consisting of a first transition series metal compound, a lithium compound, a magnesium compound, an alkali metal salt, an alkaline earth metal salt, a quaternary ammonium salt, and a quaternary phosphonium salt, is used together with a phenolic compound and the like in a solvent containing water and/or alcohol and at least one type of compound selected from the group consisting of a tin compound, an indium compound, and a rhenium compound, these compounds may also be added to a solvent containing water and/or alcohol together with at least one type of compound selected from the group consisting of a tin compound, an indium compound, and a rhenium compound. Heat treatment conditions can be appropriately regulated by a person skilled in the art depending on saccharides and alcohol types contained in raw materials. The temperature for heat treatment preferably ranges from 100° C. to 300° C., more preferably ranges from 100° C. to 250° C. For example, the temperature preferably ranges from 150° C. to 195° C.

The present invention is hereinafter described in detail with specific embodiments. However, the technical scope of the present invention is not limited to these embodiments.

(1) Method Using Tin or Organic Tin Perfluoroalkylsulfonate as a Catalyst

In an embodiment of the present invention, at least one type of tin or organic tin perfluoroalkylsulfonate is used as a catalyst for the degradation reaction of a carbohydrate-containing raw material and sugar degradation·isomerization reaction. As the "tin or organic tin perfluoroalkylsulfonate," the above compound can be used. The tin or organic tin perfluoroalkylsulfonate is preferably trifluoromethane sulfonate (trivial name: triflate). As the tin perfluoroalkylsulfonate, for example, tin (II) trifluoromethanesulfonate ($Sn(OTf)_2$) (where Tf denotes trifluoromethylsulfonyl group $CF_3SO_2-$). The same applies to the following) can be particularly preferably used. As the organic tin perfluoroalkylsulfonate, for example, dibutyltin (II) trifluoromethanesulfonate can be particularly preferably used. In one reaction system, one type of tin or organic tin perfluoroalkylsulfonate may be used and two or more types thereof may be used in combination.

A solvent containing water and/or alcohol and the amount thereof to be used in this embodiment are as defined above. In this embodiment, water may be used as a solvent when lactic acid is produced and a solvent containing alcohol may be used when lactic acid ester is produced.

The total amount of tin or organic tin perfluoroalkylsulfonate (to be used herein) to be contained in a solvent containing water and/or alcohol is not limited. A compound(s) can be used in an amount corresponding to 0.001 mol to 1.0 mol, and preferably 0.005 mol to 0.1 mol, such as 0.01 mol to 0.05 mol (in terms of mass ratio) with respect to 1 mol of glucose residue in the carbohydrate-containing raw material. When such a compound(s) is used in an excessively low amount, degradation of polysaccharides such as cellulose proceeds with difficulty, and when the same is used in an excessively high amount, the yield of lactic acid or the yield of lactic acid ester decreases because of side reactions. Such amounts are not preferred.

At least one type of compound selected from tin perfluoroalkylsulfonate and organic tin perfluoroalkylsulfonate can be preferably used as a catalyst for production of lactic acid and/or lactic acid ester from polysaccharides.

In this embodiment, tin or organic tin perfluoroalkylsulfonate can also be used in combination with at least one type of compound selected from the group consisting of a tin or organic tin halide, an indium compound and a rhenium compound as another catalyst.

In addition to at least one type of compound selected from tin perfluoroalkylsulfonate and organic tin perfluoroalkylsulfonate, at least one type of compound selected from the group consisting of a tin or organic tin halide, an indium compound, and a rhenium compound can be used as another catalyst in combination. Thus, lactic acid and/or lactic acid ester can be efficiently produced from polysaccharides and monosaccharides.

As "tin or organic tin halides," the above compounds can be used. Examples thereof include, but are not limited to, tin (II) chloride and di-n-butyltin (II) chloride.

As indium compounds, the above compounds can be used. An example thereof is, but is not limited to, indium bromide ($InBr_3$).

As rhenium compounds, the above compounds can be used. An example thereof is, but is not limited to, rhenium carbonyl ($Re_2(CO)_{10}$).

A tin or organic tin halide can be used in an amount corresponding to 0 mol to 1000 mol with respect to 1.0 mol of that of tin or organic tin perfluoroalkylsulfonate. A tin or organic tin halide is preferably used in the same amount as or higher than that of perfluoroalkylsulfonate. A tin or organic tin halide is further preferably used in an amount ranging from 1.0 mol to 50 mol (e.g., 2.0 mol to 5.0 mol) with respect to 1.0 mol of that of perfluoroalkylsulfonate.

An indium compound can be used in an amount corresponding to 0 mol to 1000 mol with respect to 1.0 mol of that of tin or organic tin perfluoroalkylsulfonate. An indium compound is preferably used in the same amount as or higher than that of tin or organic tin perfluoroalkylsulfonate. An indium compound is further preferably used in an amount ranging from 1.0 mol to 50 mol (e.g., 2.0 mol to 5.0 mol) with respect to 1.0 mol of that of perfluoroalkylsulfonate.

A rhenium compound can be used in an amount corresponding to 0 mol to 100 mol with respect to 1.0 mol of that of tin or organic tin perfluoroalkylsulfonate. A rhenium compound is further preferably used in an amount ranging from 0.01 mol to 10.0 mol (e.g., 0.1 mol to 1.0 mol) with respect to 1.0 mol of that of perfluoroalkylsulfonate.

Furthermore, in the method of the present invention, at least one type of compound selected from the group consisting of a tin or organic tin halide, an indium compound, and a rhenium compound can be used as another catalyst in combination with tin or organic tin perfluoroalkylsulfonate. Furthermore, at least one type of compound selected from the group consisting of a first transition series metal compound, a lithium compound, a magnesium compound, an alkali metal salt, an alkaline earth metal salt, a quaternary ammonium salt, and a quaternary phosphonium salt can further be used as another catalyst in combination therewith.

Lactic acid and/or lactic acid ester can be efficiently produced from polysaccharides and monosaccharides using, in addition to at least one type of compound selected from tin or organic tin perfluoroalkylsulfonate, at least one type of compound selected from the group consisting of a tin or organic tin halide, an indium compound, and a rhenium compound as another catalyst in combination, and further using a compound comprising at least one type selected from the group consisting of a first transition series metal compound, a lithium compound, a magnesium compound, an alkali metal salt, an alkaline earth metal salt, a quaternary ammonium salt, and a quaternary phosphonium salt, as another catalyst in combination.

As a first transition series metal compound, the above compound can be used. Examples thereof include, but are not limited to, manganese chloride tetrahydrate, manganese chloride tetrahydrate, cobalt chloride hexahydrate, cobalt chloride hexahydrate, nickel chloride tetrahydrate, and iron (II) chloride hexahydrate.

As a lithium compound, the above compound can be used. An example thereof is, but is not particularly limited to, lithium chloride.

As a magnesium compound, the above compound can be used. Examples thereof include, but are not limited to, magnesium chloride tetrahydrate ($MgCl_2.4H_2O$) and magnesium chloride hexahydrate ($MgCl_2.6H_2O$).

As an alkali metal salt, an alkaline earth metal salt, or a quaternary phosphonium salt, the above compound can be used. Examples thereof include, but are not limited to, bis(triphenylphosphine)iminium chloride ([PPN]Cl), bis(triphenylphosphine)iminium bromide ([PPN]Br), bis(triphenylphosphine)iminium iodine ([PPN]I), bis(triphenylphosphine)iminium carboxylic acid ([PPN]OOCH), tetraethylammonium chloride ($Et_4NCl$), triethylamine hydrochloride ($Et_3NHCl$), trioctylmethylammonium chloride ($Oct_3NMeCl$), triethyl(2-methoxyethoxymethyl)ammonium chloride ($MeOCH_2CH_2OCH_2NEt_3Cl$), 1-butyl-3-methylimidazoliumchloride ([bmim]Cl), 1-butyl-3-methylimidazoliumacetate ([bmim]OAc), 1-butyl-2,3-dimethylimidazolium chloride ([bdmim]Cl), 1-butyl-3-methylimidazoliumtetrafluoroborate ([bmim]$BF_4$), tetraphenyl phosphonium chloride ($Ph_4PCl$), lithium chloride, sodium picolinate, and sodium(trihydroxy)phenylborate.

As quaternary ammonium salts, the above compounds can be used. Examples thereof that can be more preferably used herein include, but are not limited to, bis(triphenylphosphine)iminium chloride, tetrabutylammoniumbromide, and trioctylmethylammoniumchloride.

A first transition series metal compound can be used in an amount corresponding to 0 mol to 1.0 mol with respect to 1.0 mol of tin or organic tin perfluoroalkylsulfonate. The first transition series metal compound is preferably used in the same amount as or an amount lower than that of perfluoroalkylsulfonate. The first transition series metal compound is further preferably used in an amount ranging from 0.01 mol to 0.9 mol (e.g., 0.2 mol to 0.8 mol) with respect to 1.0 mol of perfluoroalkylsulfonate.

A lithium compound is used in an amount ranging from 0.1 mol to 10.0 mol with respect to 1.0 mol of tin or organic tin perfluoroalkylsulfonate. Preferably, a lithium compound is used in an amount equivalent to or higher than that of perfluoroalkylsulfonate. Further preferably, a lithium compound is used in an amount ranging from 1.0 mol to 4.0 mol.

A magnesium compound can be used in an amount corresponding to 0 mol to 1.0 mol with respect to 1.0 mol of that of tin or organic tin perfluoroalkylsulfonate. A magnesium compound is preferably used in the same amount as or an amount lower than that of perfluoroalkylsulfonate. A magnesium compound is further preferably used in an amount ranging from 0.01 mol to 0.9 mol (e.g., 0.2 mol to 0.8 mol) with respect to 1.0 mol of perfluoroalkylsulfonate.

An alkali metal salt, an alkaline earth metal salt, or a quaternary phosphonium salt can be used in an amount corresponding to 0 mol to 100 mol with respect to 1.0 mol of that of tin or organic tin perfluoroalkylsulfonate. An alkali metal salt, alkaline earth metal salt, or quaternary phosphonium salt can be further preferably used in an amount ranging from 0.01 mol to 10.0 mol (e.g., 0.1 mol to 1.0 mol) with respect to 1.0 mol of perfluoroalkylsulfonate.

A quaternary ammonium salt is used in an amount ranging from 0.1 mol to 10.0 mol with respect to 1.0 mol of tin or organic tin perfluoroalkylsulfonate. A quaternary ammonium salt is preferably used in an amount equivalent to or higher than that of perfluoroalkylsulfonate. A quaternary ammonium salt is further preferably used in an amount ranging from 1.0 mol to 4.0 mol.

In this embodiment, when at least one type of compound selected from the group consisting of tin or organic tin perfluoroalkylsulfonate, a tin or organic tin halide, an indium compound, and a rhenium compound is used in combination with at least one type of compound selected from the group consisting of a first transition series metal compound, a lithium compound, a magnesium compound, an alkali metal salt, an alkaline earth metal salt, a quaternary ammonium salt, and a quaternary phosphonium salt, these compounds may bind to each other in a reaction solution so as to form one or more types of ate complex. As described above, an ate complex is used as a catalyst, so that retro-aldol reaction of sugars can be selectively performed while suppressing sugar cyclization, and the isomerization reaction can be efficiently performed to result in lactic acids from the carbohydrate-containing raw material.

In this embodiment, a phenolic compound can further be added to a solvent and then used in addition to at least one type of tin or organic tin perfluoroalkylsulfonate, at least one type of compound selected from the group consisting of a tin or organic tin halide, an indium compound, and a rhenium compound, and at least one type of compound selected from the group consisting of a first transition series metal compound, a lithium compound, a magnesium compound, an alkali metal salt, an alkaline earth metal salt, a quaternary ammonium salt, and a quaternary phosphonium salt. Examples of a phenolic compound include, but are not particularly limited to, catechol, 3-fluorocatechol, 2,2'-biphenol, and 3-quinolinol. The amount of the phenolic compound to be used herein can be appropriately regulated by a person skilled in the art, preferably ranging from 0.1 mol to 10.0 mol, and more preferably ranging from 1.0 mol to 4.0 mol with respect to 1.0 mol of that of each compound above.

In this embodiment, a carbohydrate-containing raw material is subjected to heat treatment in a water- and/or alcohol-containing solvent containing at least one type of tin or organic tin perfluoroalkylsulfonate. When at least one type of compound selected from the group consisting of a tin or organic tin halide, an indium compound, and a rhenium compound, a compound comprising at least one type selected from the group consisting of a first transition series metal compound, a lithium compound, a magnesium compound, an alkali metal salt, an alkaline earth metal salt, a quaternary ammonium salt, and a quaternary phosphonium salt, and a phenolic compound are used together, these compounds may be added with tin or organic tin perfluoroalkylsulfonate into a solvent containing water and/or alcohol. Heat treatment conditions can be appropriately regulated by a person skilled in the art depending on saccharides or alcohol types contained in a raw material. The temperature for heat treatment preferably ranges from 100° C. to 300° C., and more preferably ranges from 100° C. to 250° C. For example, the temperature preferably ranges from 150° C. to 195° C.

(2) Method Using a Tin Compound as a Catalyst

In another embodiment of the present invention, a carbohydrate-containing raw material is subjected to heat treatment in a water- and/or alcohol-containing solvent containing at least one type of tin compound that functions as a catalyst, so that lactic acid and/or lactic acid ester can be obtained as a reaction product. Furthermore, in this embodiment, a carbohydrate-containing raw material is subjected to heat treatment in a water- and/or alcohol-containing solvent containing, in addition to at least one type of tin compound, at least one type of compound selected from the group consisting of a lithium compound, a magnesium compound, a first transition series metal compound, and a quaternary ammonium salt, so that lactic acid and/or lactic acid ester can be obtained as a reaction product.

Through the use of this embodiment, lactic acid and/or lactic acid ester can be conveniently produced with high efficiency from carbohydrates in a carbohydrate-containing raw material, such as polysaccharides (e.g., cellulose, starch, and oligosaccharide) and monosaccharides (e.g., fructose), even if a relatively low reaction temperature is used.

A carbohydrate-containing raw material that can be used as a raw material in this embodiment may be any raw material containing saccharides. The above-defined raw material can be used as such a carbohydrate-containing raw material, but the example is not limited thereto.

In the method of the present invention, at least one type of tin compound is used as a catalyst for degradation reaction of polysaccharides, and sugar degradation•isomerization reaction.

In the method of the present invention, the above compounds can be used as the "tin compound(s)." Examples thereof that can be particularly preferably used include, but are not particularly limited to, tin (II) chloride, tin (IV) chloride (tin chloride pentahydrate), tin (II) bromide, n-butyltin (II) chloride, phenyltin trichloride, tin (II) trifluoromethanesulfonate ($Sn(OTf)_2$), and dibutyltin (II) trifluoromethanesulfonate ($^nBu_2Sn(OTf)_2$).

In one reaction system, one type of tin compound may be used and two or more types thereof may be used in combination.

In the method of the present invention, at least one type of compound selected from the group consisting of a lithium compound, a magnesium compound, a first transition series metal compound, and a quaternary ammonium salt can be further used as another catalyst for degradation reaction of cellulose, and sugar degradation•isomerization reaction.

As "a lithium compound, a magnesium compound, and a first transition series metal compound," the above compounds can be used. Preferable examples thereof include fluorides, chlorides, bromides, and iodides of lithium, magnesium, and first transition series metals (that is, scandium, titanium, vanadium, chromium, manganese, iron, cobalt, nickel, copper, and zinc). Further preferable examples thereof are chlorides. Examples thereof that can be particularly preferably used include, but are not particularly limited to, lithium chloride, manganese chloride tetrahydrate, cobalt chloride hexahydrate, cobalt chloride hexahydrate, nickel chloride tetrahydrate, and iron (II) chloride hexahydrate.

As "quaternary ammonium salt(s)," the above compounds can be used. Examples thereof include, but are not particularly limited to, quaternary ammonium salt halides (fluorides, chlorides, bromides, and iodides). Examples of such a quaternary ammonium salt halide that can be particularly preferably used herein include, but are not limited to, bis(triphenylphosphine)iminium chloride, tetrabutylammoniumbromide, and trioctylmethylammoniumchloride.

Also, in this embodiment, an alkali metal salt, an alkaline earth metal salt, a quaternary phosphonium salt, or the like can also be used in addition to or instead of at least one type of compound selected from the group consisting of a lithium compound, a magnesium compound, a first transition series metal compound, and a quaternary ammonium salt. As an alkali metal salt, an alkaline earth metal salt, and a quaternary phosphonium salt, the above compounds can be used. Examples thereof include, but are not limited to, bis(triphenylphosphine)iminium chloride ([PPN]Cl), bis(triphenylphosphine)iminium bromide ([PPN]Br), bis(triphenylphosphine)iminium iodine ([PPN]I), bis(triphenylphosphine)iminium carboxylic acid ([PPN]OOCH), tetraethylammonium chloride ($Et_4NCl$), triethylamine hydrochloride ($Et_3NHCl$), trioctylmethylammonium chloride ($Oct_3NMeCl$), triethyl(2-methoxyethoxymethyl)ammonium chloride ($MeOCH_2CH_2OCH_2NEt_3Cl$), 1-butyl-3-methylimidazoliumchloride ([bmim]Cl), 1-butyl-3-methylimidazoliumacetate ([bmim]OAc), 1-butyl-2,3-dimethylimidazolium chloride ([bdmim]Cl), 1-butyl-3-methylimidazoliumtetrafluoroborate ([bmim]$BF_4$), tetraphenyl phosphonium chloride ($Ph_4PCl$), lithium chloride, sodium picolinate, and sodium(trihydroxy)phenylborate.

In one reaction system, one type of compound selected from the group consisting of a lithium compound, a magnesium compound, a first transition series metal compound, and a quaternary ammonium salt, an alkali metal salt, an alkaline earth metal salt, and a quaternary phosphonium salt may be used and two or more types thereof may be used in combination.

A solvent containing water and/or alcohol and the amount of the same to be used in the method of this embodiment are as defined above.

The total amount of a tin compound(s) (to be used herein as a catalyst) to be contained in a solvent containing water and/or alcohol is not limited. A tin compound(s) can be used in an amount corresponding to 0.001 mol to 1.0 mol, and preferably 0.005 mol to 0.1 mol, such as 0.01 mol to 0.05 mol (in terms of mass ratio) with respect to 1 mol of glucose residue or fructose residue in the carbohydrate-containing raw material. When such a tin compound(s) is used in an excessively low amount, degradation reaction of cellulose and sugar degradation•isomerization reaction proceed with difficulty, and when the same is used in an excessively high amount, the yield of lactic acid of interest decreases because of side reactions. Such amounts are not preferred.

The amount of at least one type of compound selected from the group consisting of a lithium compound, a magnesium compound, a first transition series metal compound, a quaternary ammonium salt, an alkali metal salt, an alkaline earth metal salt, and a quaternary phosphonium salt, which is used in addition to a tin compound and used can be appropriately regulated by a person skilled in the art, ranging from 0.1 mol to 10.0 mol, preferably being equivalent to or higher than, and further preferably ranging from 1.0 mol to 4.0 mol, with respect to 1.0 mol of that of the tin compound to be used as a catalyst.

In this embodiment, when a tin compound and a promoter are used in combination, these compounds may bind to each other in a reaction solution so as to form one or more types of ate complex. An ate complex is used as a catalyst as described above so that: retro-aldol reaction of sugar can be selectively caused to proceed while suppressing sugar cyclization; and the isomerization reaction can be efficiently caused to proceed to result in lactic acids from the carbohydrate-containing raw material.

In this embodiment, a carbohydrate-containing raw material is subjected to heat treatment in a water- and/or alcohol-containing solvent containing a tin compound and at least one type of compound selected from a lithium compound, a magnesium compound, a first transition series metal compound, a quaternary ammonium, an alkali metal salt, an alkaline earth metal salt, and a quaternary phosphonium salt. Heat treatment conditions can be appropriately regulated by a person skilled in the art depending on saccharides or alcohol types contained in a raw material. The temperature for heat treatment preferably ranges from 100° C. to 300° C., and more preferably ranges from 100° C. to 250° C. For example, the temperature preferably ranges from 150° C. to 160° C. In this embodiment, heat treatment can be performed at such a relatively low temperature.

(3) Method Using a Rhenium Compound as a Catalyst

In another embodiment of the present invention, a carbohydrate-containing raw material is subjected to heat treatment in a water- and/or alcohol-containing solvent containing a rhenium compound functioning as a catalyst, so that lactic acid and/or lactic acid ester can be obtained as a reaction product.

Through the use of this embodiment, lactic acid and/or lactic acid ester can be conveniently produced with high efficiency from carbohydrates in a carbohydrate-containing raw material, such as polysaccharides (e.g., cellulose), monosaccharides (e.g., fructose), or oligosaccharides even when a relatively low reaction temperature is used.

A carbohydrate-containing raw material that can be used as a raw material in this embodiment may be any raw material containing carbohydrates. The above-defined raw materials can be used herein, but the examples are not limited thereto.

In this embodiment, at least one type of rhenium compound is used as a catalyst for degradation reaction of cellulose, and/or sugar degradation•isomerization reaction. In this embodiment, examples of a "rhenium compound" include halides (including fluorides, chlorides, bromides, and iodides), an acetylacetone compound, an alkoxide compound, a carboxylate compound, a carbonyl compound, a phosphate compound, a sulfate compound, and a nitrate compound. A rhenium compound preferably contains a carbonyl ligand and an example thereof is, but is not particularly limited to, rhenium carbonyl. In one reaction system, one type of rhenium compound may be used and two or more types of the same may also be used in combination.

A solvent containing water and/or alcohol and the amount of the same to be used in this embodiment are as defined above.

The total amount of a rhenium compound (to be used herein) to be contained in a solvent containing water and/or alcohol is not limited. A rhenium compound(s) can be used in an amount corresponding to 0.001 mol to 100.0 mol, and preferably 0.005 mol to 10.0 mol, such as 0.01 mol to 0.1 mol (in terms of mass ratio) with respect to 1 mol of glucose residue or fructose residue in the carbohydrate-containing raw material. When such a compound(s) is used in an excessively low amount, degradation reaction of cellulose and sugar degradation•isomerization reaction proceed with difficulty. Such amounts are not preferred.

In this embodiment, a compound of a metal other than rhenium can also be used in combination with a rhenium compound. Examples of a "compound of a metal other than rhenium" in the method of the present invention include halides (including fluorides, chlorides, bromides, and iodides) of magnesium, tin, or first transition series metals (that is, scandium, titanium, vanadium, chromium, manganese, iron, cobalt, nickel, copper, and zinc), an acetylacetone compound, an alkoxide compound, a carboxylate compound, a carbonyl compound, a phosphate compound, a sulfate compound, a nitrate compound, and perfluoroalkylsulfonate.

Examples of a magnesium compound that can be used in this embodiment include, but are not particularly limited to, a magnesium halide (including hydrate) and magnesium perfluoroalkylsulfonate. An example of a magnesium halide is magnesium chloride hexahydrate that can be particularly preferably used. Examples of "magnesium perfluoroalkylsulfonate" as used herein include, but are not particularly limited to, trifluoromethane sulfonate, pentafluoromethane sulfonate, heptafluoropropane sulfonate, and nonafluorobutane sulfonate. In this embodiment, a more preferable example of perfluoroalkylsulfonate is trifluoromethane sulfonate (trivial name: triflate). An example of magnesium perfluoroalkylsulfonate that can be particularly preferably used herein is magnesium trifluoromethanesulfonate (magnesium triflate: $Mg(OTf)_2$) (Tf denotes a trifluoromethylsulfonyl group $CF_3SO_2$—). The same applies to the following).

As tin compounds that can be used in this embodiment, the above compounds can be used. Examples thereof that can be particularly preferably used in this embodiment include, but are not particularly limited to, tin (II) chloride and di-n-butyltin (II) chloride.

As first transition series metal compounds that can be used in this embodiment, the above compounds can be used. Examples thereof that can be particularly preferably used herein include, but are not particularly limited to, manganese chloride tetrahydrate ($MnCl_2 \cdot 4H_2O$), iron (II) chloride hexahydrate b ($FeCl_2 \cdot 6H_2O$), cobalt chloride hexahydrate ($CoCl_2 \cdot 6H_2O$), and nickel chloride tetrahydrate ($NiCl_2 \cdot 4H_2O$).

Also, in this embodiment, as a "compound of a metal other than rhenium," an alkali metal salt, an alkaline earth metal salt, a quaternary phosphonium salt, a quaternary ammonium salt, and the like can also be used in addition to or instead of the above compounds. As an alkali metal salt, an alkaline earth metal salt, a quaternary phosphonium salt, and the above compounds can be used. Examples thereof include, but are not limited to, bis(triphenylphosphine)iminium chloride ([PPN]Cl), bis(triphenylphosphine)iminium bromide ([PPN]Br), bis(triphenylphosphine) iminium iodine ([PPN]I), bis(triphenylphosphine) iminium carboxylic acid ([PPN]OOCH), tetraethylammonium chloride ($Et_4NCl$), triethylamine hydrochloride ($Et_3NHCl$), trioctylmethylammonium chloride ($Oct_3NMeCl$), triethyl(2-methoxyethoxymethyl)ammonium chloride ($MeOCH_2CH_2OCH_2NEt_3Cl$), 1-butyl-3-methylimidazolium chloride ([bmim]Cl), 1-butyl-3-methylimidazolium acetate ([bmim]OAc), 1-butyl-2,3-dimethylimidazolium chloride ([bdmim]Cl), 1-butyl-3-methylimidazoliumtetrafluoroborate ([bmim]$BF_4$), tetraphenylphosphonium chloride ($Ph_4PCl$), lithium chloride, sodium picolinate, sodium(trihydroxy)phenylborate, bis(triphenylphosphine)iminium chloride, tetrabutylammoniumbromide, and trioctylmethylammonium chloride.

In one reaction system, a rhenium compound and one or a plurality of types of compound of a metal other than rhenium may be used in combination.

In this embodiment, when a rhenium compound is used in combination with a compound(s) of a metal other than rhenium, these compounds may bind in a reaction solution so as to form a metal compound containing two or more types of metal (containing rhenium and a metal other than rhenium). Alternatively, a metal compound containing two or more types of metal (containing rhenium and a metal other than rhenium) may be synthesized in advance and then added to a reaction solution. The thus generated metal compound functions as a catalyst for the above degradation reaction of cellulose and/or sugar degradation·isomerization reaction. An example of such a metal compound containing two or more types of metal (containing rhenium and a metal other than rhenium) that can be particularly preferably used herein is, but is not particularly limited to, a rhenium carbonyl complex. Also, in this embodiment, when a rhenium compound is used in combination with a compound of a metal other than rhenium, these compounds may bind in a reaction solution so as to form one or more types of ate complex. Here, the term "ate complex" refers to a complex-type metal acid salt generated by coordination of anionic species (supplied from a compound of a metal other than rhenium) into a rhenium compound having Lewis acidity.

An ate complex is used as a catalyst, so that selective retro-aldol reaction of sugars can be caused to proceed while suppressing sugar cyclization, as described above. Furthermore, the isomerization reaction can be efficiently caused to proceed to result in lactic acids from the carbohydrate-containing raw material.

When a compound of a metal other than rhenium is used, the amount of such a compound to be used herein can be appropriately regulated by a person skilled in the art, ranging from 0.1 mol to 10.0 mol with respect to, preferably being equivalent to or higher than, and further preferably ranging from 1.0 mol to 4.0 mol with respect to, 1.0 mol of that of a rhenium compound.

This embodiment can also be performed in the presence of tin or organic tin perfluoroalkylsulfonate. Specifically, this embodiment is performed in the presence of tin or organic tin perfluoroalkylsulfonate, so that the yields of lactic acids can be further increased compared with a case in which a rhenium compound alone or a combination of a rhenium compound and a compound of a metal other than rhenium. "Tin or organic tin perfluoroalkylsulfonate" may be either tin (II) salt or tin (IV) salt. As perfluoroalkylsulfonate, trifluoromethanesulfonate is preferred. For example, tin (II) trifluoromethanesulfonate ($Sn(OTf)_2$), dibutyltin(II) trifluoromethanesulfonate ($^nBu_2Sn(OTf)_2$), and the like can be particularly preferably used.

When tin or organic tin perfluoroalkylsulfonate is used, the amount of the same to be used herein can be appropriately regulated by a person skilled in the art. The amount of tin or organic tin perfluoroalkylsulfonate can be selected from the range of amounts equivalent to or higher than that of a rhenium compound, ranging from preferably 1.0 mol to 4.0 mol with respect to 1.0 mol of that of a rhenium compound.

In this embodiment, a carbohydrate-containing raw material is subjected to heat treatment in a water- and/or alcohol-containing solvent containing a rhenium compound. When a compound of a metal other than rhenium or tin or organic tin perfluoroalkylsulfonate is also used together, the metal compound other than rhenium or tin or organic tin perfluoroalkylsulfonate may also be added with a rhenium compound into a solvent containing water and/or alcohol. Alternatively, after synthesis of the above metal compound containing two or more types of metal (rhenium and a metal other than rhenium) from a rhenium compound and a compound of a metal other than rhenium, the metal compound containing two or more types of metal (rhenium and a metal other than rhenium) may be added to a solvent containing water and/or alcohol. Heat treatment conditions can be appropriately regulated by a person skilled in the art depending on saccharides or alcohol types contained in a raw material. The temperature for heat treatment preferably ranges from 100° C. to 300° C., and more preferably ranges from 100° C. to 250° C. For example, the temperature preferably ranges from 150° C. to 200° C.

(4) Method Using an Indium Compound and the Like as Catalysts

In another embodiment of the present invention, a carbohydrate-containing raw material is subjected to heat treatment in a water- and/or alcohol-containing solvent containing at least one type of metal compound that functions as a catalyst and is selected from the group consisting of an indium compound, a gallium compound, an aluminium compound, a tin compound, and a rhenium compound, so that lactic acid and/or lactic acid ester can be obtained as a reaction product. Furthermore, in this embodiment, a carbohydrate-containing raw material is subjected to heat treatment in a water- and/or alcohol-containing solvent containing at least one type of compound selected from the group consisting of an alkali metal salt, an alkaline earth metal salt, a first transition series metal salt, a quaternary ammonium salt, and a quaternary phosphonium salt in addition to at least one type of the above compound, so that lactic acid and/or lactic acid ester can be obtained as a reaction product.

Through the use of this embodiment, lactic acid and/or lactic acid ester can be conveniently produced with high efficiency from carbohydrates, such as polysaccharides (e.g., starch and oligosaccharide) and monosaccharides (e.g., fructose) in a carbohydrate-containing raw material, even when a relatively low reaction temperature is used.

A carbohydrate-containing raw material that can be used as a raw material in this embodiment may be any raw material containing carbohydrates. The above-defined raw materials can be used, but the examples thereof are not limited thereto.

In this embodiment, at least one type of metal compound selected from the group consisting of an indium compound, a gallium compound, an aluminium compound, a tin compound, and a rhenium compound is used as a catalyst for the degradation reaction of polysaccharides, and sugar degradation•isomerization reaction.

As "indium compound," "tin compound," and "rhenium compound" in this embodiment, the above-defined compounds can be used. Examples thereof are preferably halide salts and carboxylate. Examples of such metal compounds include, but are not limited to, indium (III) bromide, indium (III) chloride, indium (III) iodide, indium (III) chloride tetrahydrate, indium (III) acetate, acetylacetone indium (III), tin (II) chloride, di-n-butyltin (II) chloride, and rhenium carbonyl.

Examples of "a gallium compound" and "an aluminium compound" in this embodiment include halide salts of these metals (fluorides, chlorides, bromides, and iodides), an acetylacetone compound, an alkoxide compound, carboxylate, phosphate, sulfate, and nitrate. Preferable examples thereof include halide salts and carboxylate. Specific examples thereof include, but are not limited to, gallium (III) trichloride and aluminium (III) chloride hexahydrate.

In one reaction system, at least one type of compound selected from the group consisting of an indium compound, a gallium compound, an aluminium compound, a tin compound, and a rhenium compound may be used and two or more of these compounds may be used in combination.

In this embodiment, at least one type of compound selected from the group consisting of an alkali metal salt, an alkaline earth metal salt, a first transition series metal salt, a quaternary ammonium salt, and a quaternary phosphonium salt is used as another catalyst for degradation reaction of cellulose, and sugar degradation•isomerization reaction.

Regarding "an alkali metal salt, an alkaline earth metal salt, a first transition series metal salt, a quaternary ammonium salt, and a quaternary phosphonium salt," the above compounds can be used as an alkali metal salt, an alkaline earth metal salt, and a quaternary phosphonium salt. Examples thereof include, but are not limited to, bis(triphenylphosphine)iminium chloride ([PPN]Cl), bis(triphenylphosphine)iminium bromide ([PPN]Br), bis(triphenylphosphine)iminium iodine ([PPN]I), bis(triphenylphosphine)iminium carboxylic acid ([PPN]OOCH), tetraethylammonium chloride ($Et_4NCl$), triethylamine hydrochloride ($Et_3NHCl$), trioctylmethylammonium chloride ($Oct_3NMeCl$), triethyl(2-methoxyethoxymethyl)ammonium chloride ($MeOCH_2CH_2OCH_2NEt_3Cl$), 1-butyl-3-methylimidazoliumchloride ([bmim]Cl), 1-butyl-3-methylimidazoliumacetate ([bmim]OAc), 1-butyl-2,3-dimethylimidazolium chloride ([bdmim]Cl), 1-butyl-3-methylimidazoliumtetrafluoroborate ([bmim]$BF_4$), tetraphenyl phosphonium chloride ($Ph_4PCl$), lithium chloride, sodium picolinate, sodium(trihydroxy)phenylborate, bis(triphenylphosphine)iminium chloride, tetrabutylammoniumbromide, and trioctylmethylammonium chloride.

In one reaction system, one type of compound selected from the group consisting of an alkali metal salt, an alkaline earth metal salt, a first transition series metal salt, a quaternary ammonium salt, and a quaternary phosphonium salt may be used and two or more of these salts may be used in combination.

A solvent containing water and/or alcohol and the amount of the same to be used in this embodiment are as defined above.

The total amount (to be used herein) of at least one type of compound selected from the group consisting of an indium compound, a gallium compound, an aluminium compound, a tin compound, and a rhenium compound to be contained as a catalyst in a solvent containing water and/or alcohol is not limited. A compound(s) can be used in an amount corresponding to 0.001 mol to 1.0 mol, and preferably 0.005 mol to 0.1 mol, such as 0.01 mol to 0.05 mol (in terms of mass ratio) with respect to 1 mol of glucose residue or fructose residue in the carbohydrate-containing raw material.

The amount of at least one type of compound selected from the group consisting of an alkali metal salt, an alkaline earth metal salt, a first transition series metal salt, a quaternary ammonium salt, and a quaternary phosphonium salt to be used as another catalyst can be appropriately regulated by a person skilled in the art, ranging from 0.1 mol to 10.0 mol with respect to 1.0 mol of that of a compound selected from an indium compound, a gallium compound, an aluminium compound, a tin compound, and a rhenium compound to be used as a catalyst. The amount is further preferably equivalent to or higher than 1.0 mol of that of a compound selected from an indium compound, a gallium compound, an aluminium compound, a tin compound, and a rhenium compound, and further preferably ranges from 1.0 mol to 4.0 mol.

In this embodiment, when a compound selected from an indium compound, a gallium compound, an aluminium compound, a tin compound, and a rhenium compound is used in combination with a compound selected from an alkali metal salt, an alkaline earth metal salt, a first transition series metal salt, a quaternary ammonium salt, and a quaternary phosphonium salt, these compounds may bind in a reaction solution so as to form one or more types of ate complex. The term "ate complex" refers to a complex-type metal acid salt generated by coordination of anionic species (supplied from a compound(s) selected from an alkali metal salt, an alkaline earth metal salt, a first transition series metal salt, a quaternary ammonium salt, and a quaternary phosphonium salt) to a compound selected from an indium compound, a gallium compound, an aluminium compound, a tin compound, and a rhenium compound having Lewis acidity.

An ate complex is used as a catalyst, so that selective retro-aldol reaction of sugars can be performed while suppressing sugar cyclization, as described above. Furthermore, the isomerization reaction can be efficiently performed to result in lactic acids from the carbohydrate-containing raw material.

In this embodiment, tin or organic tin perfluoroalkylsulfonate can be used as another catalyst in combination with at least one type of metal compound selected from the group consisting of an indium compound, a gallium compound, an aluminium compound, a tin compound, and a rhenium compound, and at least one type of salt selected from the group consisting of an alkali metal salt, an alkaline earth metal salt, a first transition series metal salt, a quaternary ammonium salt, and a quaternary phosphonium salt. Tin or organic tin perfluoroalkylsulfonate can be used as a catalyst for degradation reaction of polysaccharides such as cellulose and sugar degradation•isomerization reaction. Therefore, tin or organic tin perfluoroalkylsulfonate is particularly preferable when a carbohydrate-containing raw material contains polysaccharides such as cellulose.

As tin or organic tin perfluoroalkylsulfonate, the above compound can be used. A preferable example thereof is trifluoromethanesulfonate (trivial name: triflate). For example, tin (II) trifluoromethanesulfonate and dibutyltin (II) trifluoromethanesulfonate can be used.

Tin or organic tin perfluoroalkylsulfonate can be used in an amount corresponding to 0 mol to 1000 mol with respect to 1.0 mol of that of a compound selected from an indium compound, a gallium compound, an aluminium compound, a tin compound, and a rhenium compound. Tin or organic tin perfluoroalkylsulfonate is preferably used in the same amount as or higher than that of a compound selected from an indium compound, a gallium compound, an aluminium compound, a tin compound, and a rhenium compound. Tin or organic tin perfluoroalkylsulfonate is further preferably used in an amount ranging from 1.0 mol to 50 mol (e.g., 1.0 mol to 20 mol) with respect to 1.0 mol of that of a compound selected from an indium compound, a gallium compound, an aluminium compound, a tin compound, and a rhenium compound.

In this embodiment, a carbohydrate-containing raw material is subjected to heat treatment in a water- and/or alcohol-containing solvent containing at least one type of compound selected from an indium compound, a gallium compound, an aluminium compound, a tin compound, and a rhenium compound and at least one type of compound selected from an alkali metal salt, an alkaline earth metal salt, a first transition series metal salt, a quaternary ammonium salt, and a quaternary phosphonium salt, and further containing tin or organic tin perfluoroalkylsulfonate if necessary. Heat treatment conditions can be appropriately regulated by a person skilled in the art depending on saccharides and alcohol types contained in raw materials. The temperature for heat treatment preferably ranges from 100° C. to 300° C., and more preferably ranges from 100° C. to 250° C. For example, the temperature preferably ranges from 150° C. to 160° C. According to the method of the present invention, heat treatment can be performed at a relatively low temperature.

(5) Method Using Indium Alkoxide and the Like as Catalysts

In still another embodiment of the present invention, a carbohydrate-containing raw material is subjected to heat treatment in a water- and/or alcohol-containing solvent containing at least one type that functions as a catalyst and is selected from the group consisting of indium alkoxide and indium acetylacetonate, so that a reaction product containing lactic acid and/or lactic acid ester can be obtained.

Through the use of this embodiment, lactic acid and/or lactic acid ester can be conveniently produced with very high efficiency from carbohydrates in a carbohydrate-containing raw material.

A carbohydrate-containing raw material that can be used as a raw material in this embodiment may be any raw material containing carbohydrates. The above-defined materials can be used herein, but the examples thereof are not limited thereto.

In this embodiment, indium alkoxide or indium acetylacetonate is used as a catalyst for degradation reaction and isomerization reaction for a carbohydrate-containing raw material and isomerization reaction of triose (generated as an intermediate) to result in lactic acid and/or lactic acid ester. In a preferred example of this embodiment, indium alkoxide is preferably used. In another example of this embodiment, indium acetylacetonate is preferably used. In still another example of this embodiment, both indium acetylacetonate and indium alkoxide may be used. Examples of indium alkoxide that can be used in this embodiment include indium methoxide, indium ethoxide, indium isopropoxide, indium-n-butoxide, and indium-t-butoxide. Examples of indium acetylacetonate that can be used in this embodiment include acetylacetone indium, tris(2,2,6,6-tetramethyl-3,5-heptanedionate)indium, and indium trifluoroacetylacetonate. In one reaction system, one type of indium alkoxide and indium acetylacetonate may be used and two or more types thereof may be used.

A solvent containing water and/or alcohol and the amount of the same to be used in this embodiment are as defined above.

The total amount (to be used herein) of indium alkoxide and/or indium acetylacetonate, which is to be contained in a solvent containing water and/or alcohol is as follows. Indium alkoxide and/or indium acetylacetonate can be used in an amount corresponding to 0.00001 mol to 1.0 mol, and preferably 0.005 mol to 0.1 mol (e.g., 0.01 mol to 0.05 mol) in terms of mass ratio with respect to 1 mmol of glucose residue in a carbohydrate-containing raw material. However, the examples thereof are not limited thereto.

A method for producing lactic acids using indium alkoxide and/or indium acetylacetonate is particularly suitable for generation of lactic acids from monosaccharides, and thus is particularly preferable when a carbohydrate-containing raw material contains monosaccharides.

In this embodiment, a phenolic compound is preferably further added to a solvent and then used, in addition to indium alkoxide and/or indium acetylacetonate. Examples of a phenolic compound include, but are not particularly limited to, phenol, cresol, alkylphenol, catechol, pyrogallol, alkoxyphenol, salicylic acid, salicylic acid ester, 2,2'-biphenol, and quinolinol. The amount of a phenolic compound to be used herein can be appropriately regulated by a person skilled in the art, preferably ranging from 0.1 mol to 10.0 mol and further preferably ranging from 1.0 mol to 4.0 mol with respect to 1.0 mol of the total amount (to be used herein) of indium alkoxide and/or indium acetylacetonate. The yields of lactic acids can be significantly improved by the addition of a phenolic compound.

In this embodiment, a carbohydrate-containing raw material is subjected to heat treatment in a water- and/or alcohol-containing solvent containing indium alkoxide and/or indium acetylacetonate. In this embodiment, indium alkoxide and/or indium acetylacetonate, and a carbohydrate-containing raw material are preferably added into a solvent containing water and/or alcohol before heat treatment. A phenolic compound may be added with indium alkoxide and/or indium acetylacetonate to the solvent containing water and/or alcohol. Heat treatment conditions can be appropriately regulated by a person skilled in the art depending on saccharides or alcohol types contained in a raw material. The temperature for heat treatment preferably ranges from 100° C. to 300° C., and more preferably ranges from 100° C. to 250° C. For example, the temperature preferably ranges from 140° C. to 195° C.

All embodiments (1) to (5) above can be performed at a relatively low temperature for heating. The heat treatment is also preferably performed in the absence of oxygen. To create such oxygen-free conditions, preferably, a reactor is filled with an inert gas before heat treatment and then air is purged (eliminated). Inert gas types are not particularly limited. Examples of inert gas include nitrogen gas, argon gas, and carbon dioxide gas. Heat treatment is also preferably performed under pressurized conditions. The reaction pressure is preferably the same as or higher than atmospheric pressure, preferably ranging from 0.3 MPa to 20 MPa and further preferably ranging from 0.4 MPa to 10 MPa.

In embodiments (1) to (5) above, reaction in a solvent containing water and/or alcohol is preferably performed in an autoclave, for example, but the example thereof is not limited thereto. Another preferable reaction form is a continuous flow-based reaction method (continuous method). A reaction solution prepared by mixing a raw material, a solvent, and a catalyst is continuously supplied to a reactor controlled to have a predetermined temperature and pressure, and caused to remain within a reactor for a predetermined time for reaction.

In embodiments (1) to (5) above, for example, at least one type of compound selected from the group consisting of a tin compound, a rhenium compound, and an indium compound, and if necessary another compound (at least one type of compound selected from the group consisting of a magnesium compound, a first transition series metal compound, a lithium compound, an alkali metal salt, an alkaline earth metal salt, a first transition series metal salt, a quaternary ammonium salt, a quaternary phosphonium salt, and a phenolic compound), a carbohydrate-containing raw material, and a water- and/or alcohol-containing solvent are placed in an electromagnetic stirring autoclave. Air is purged with inert gas, the resultant is heated to the above temperature for heating, and thus reaction is performed for a predetermined time. The time for heating can be appropriately regulated by a person skilled in the art. Examples thereof range from, but are not particularly limited to, 3 hours to 24 hours after the temperature has reached the temperature for heating and preferably range from 5 hours to 12 hours. After the predetermined time for heating has passed, heating is halted and then the resultant is left to stand to cool to room temperature. After it is cooled to room temperature, the reaction product is removed from the autoclave.

Also, when a continuous flow-based reaction method is employed, a reaction solution prepared by mixing at least one type of compound selected from the group consisting of a tin compound, a rhenium compound, and an indium compound, another compound if necessary (at least one type of compound selected from the group consisting of a magnesium compound, a first transition series metal compound, a lithium compound, an alkali metal salt, an alkaline earth metal salt, a first transition series metal salt, a quaternary ammonium salt, a quaternary phosphonium salt, and a phenolic compound), a carbohydrate-containing raw material, and a solvent containing water and/or alcohol is continuously supplied to a reactor controlled to have a predetermined temperature for heating and pressure. The resultant is caused to remain within the reactor for a predetermined time for heating for reaction. After the time for heating has passed, heating is halted and then the resultant is left to stand to cool to room temperature. After it has been cooled to room temperature, the reaction product is removed from the reactor.

With the above method, lactic acid and/or lactic acid ester can be generated in a high yield. When a carbohydrate-containing raw material contains cellulose, lactic acids are generated in large amounts from saccharides resulting from efficient solvolysis of cellulose. According to the method of the present invention, lactic acid and/or lactic acid ester can be obtained with a yield of 9% to 50% on the basis of the number of moles of lactic acid and/or lactic acid ester generated per glucose residue or fructose residue in a carbohydrate-containing raw material. In addition, yield is given in percentage (%) figures, representing the number of moles (mol) of lactic acid and/or lactic acid ester with respect to the number of moles of lactic acids theoretically generated per glucose residue (lactic acids/glucose residue=2 mol/1 mol) or per fructose residue (lactic acids/fructose residue=5 mol/2.5 mol) from cellulose as a raw material.

In particular, when a solvent used in the above "(1) Method using tin or organic tin perfluoroalkylsulfonate as a catalyst" contains alcohol, lactic acid and/or lactic acid ester can be obtained with a yield of about 20% to 40%, for example, on the basis of yield (%) per glucose residue or fructose residue in a carbohydrate-containing raw material. When a tin compound (in particular, a tin or organic tin halide such as tin chloride or di-n-butyltin chloride) other than perfluoroalkylsulfonate is used in addition to tin or organic tin perfluoroalkylsulfonate, the yield of lactic acid and/or lactic acid ester can be increased by 1% to 10%, for example, compared with a case in which tin or organic tin perfluoroalkylsulfonate is used alone. Furthermore, when one or more types of compound selected from the group consisting of an indium compound (and in particular, indium halide), a rhenium compound, a magnesium compound, and a first transition series metal compound are used in addition to tin or organic tin perfluoroalkylsulfonate, the yield of lactic acid and/or lactic acid ester can be increased by about 1% to 20%, for example, compared with a case in which tin or organic tin perfluoroalkylsulfonate is used alone or a case in which a tin compound other than perfluoroalkylsulfonate (in particular, a tin or organic tin halide such as tin chloride or di-n-butyltin chloride) in addition to tin or organic tin perfluoroalkylsulfonate. Furthermore, when tin or organic tin perfluoroalkylsulfonate alone is used, when a tin compound other than perfluoroalkylsulfonate (and in particular, a tin or organic tin halide such as tin chloride or di-n-butyltin chloride) is used in addition to tin or organic tin perfluoroalkylsulfonate, or when one or more types of compound selected from the group consisting of an indium compound (in particular, an indium halide), a rhenium compound, a magnesium compound, and a first transition series metal compound are further used in addition to a phenolic compound, the yield of lactic acid and/or lactic acid ester can be increased by about 1% to 20%, for example, compared with a case of adding no phenol compound.

Also, according to the above "(2) Method using a tin compound as a catalyst," lactic acids can be obtained with yields of about 45% to 60% on the basis of yield (%) per glucose residue or fructose residue in a carbohydrate-containing raw material containing cellulose, monosaccharides, or the like.

Furthermore, according to the above "(3) Method using a rhenium compound as a catalyst," when a rhenium compound alone is used, lactic acids (e.g., lactic acid ester) can be obtained with yields of 15% to 30% on the basis of the number of moles of lactic acids generated per glucose residue or fructose residue in a carbohydrate-containing raw material containing cellulose, monosaccharides, or the like. Also, when a compound of a metal other than rhenium or tin or organic tin perfluoroalkylsulfonate is used in addition to a rhenium compound, the yields of lactic acids can be increased by 5% to 50%, for example, compared with a case in which a rhenium compound is used alone.

Furthermore, according to "(4) Method using an indium compound and the like as catalysts" above, an alkali metal salt or the like is used in addition to an indium compound or the like, lactic acids can be obtained with a yield of 15% to 75% (e.g., yield of 50% to 70%) on the basis of the number of moles of lactic acids generated per glucose residue in a carbohydrate-containing raw material.

Furthermore, according to "(5) Method using an indium alkoxide and the like as catalysts" above, lactic acid and/or lactic acid ester can be obtained with a yield of 5% to 60% (e.g., yield of 30% to 50%) on the basis of the number of moles of lactic acid and/or lactic acid ester generated per glucose residue in a carbohydrate-containing raw material. When a phenolic compound is used in combination with indium alkoxide and/or indium acetylacetonate, the yield of lactic acid and/or lactic acid ester can be increased by 5% to 15%, for example, compared with a case in which indium alkoxide and/or indium acetylacetonate is used alone. When a phenolic compound is used in combination with indium alkoxide and/or indium acetylacetonate, the yield of lactic acid and/or lactic acid ester can be increased by 5% to 15%, for example, compared with a case in which indium alkoxide and/or indium acetylacetonate is used alone.

Lactic acid or lactic acid ester is also preferably separated from the above-obtained reaction solution. Such separation can be performed by an organic acid separation method known by a person skilled in the art, such as liquid chromatography.

The method of the present invention is useful since the yield of lactic acid ester can be improved by the method while suppressing the amount of acid to be used as a catalyst to a low level.

EXAMPLES

Hereafter, the present invention is described in greater detail with reference to the examples, although the technical scope of the present invention is not limited to the examples.

(1) Method Using a Tin Compound as a Catalyst

Example 1

Cellulose (0.405 g) (corresponding to 2.5 mmol of glucose residue) that had been dried for 2 or more hours in air at 120° C., 8 mg (0.02 mmol) of tin (II) trifluoromethanesulfonate $(Sn(OTf)_2; Tf=CF_3SO_2)$, 20 mL of methanol, and a stirring bar were added to a 50-mL stainless-steel autoclave, and then the lid was closed. Air in the autoclave was purged with nitrogen gas. After pressurization to 0.5 MPa, the interior of the autoclave was heated to 190° C. using a mantle heater while stirring the mixture with a magnetic stirrer. Subsequently, stirring was continued for 10 hours while maintaining a temperature of 190° C., heating was then stopped, and then the autoclave was left to cool at room temperature. The reaction solution was removed from the autoclave after cooling to room temperature, and various products in the solution were quantitatively analyzed by liquid chromatography. The yields of lactic acids in the analytical results are shown in Table 1 below. Each yield is represented in percentage (%) figures for the number of moles (mol) of each product with respect to the number of moles (lactic acids/glucose residue=5 mmol/2.5 mmol) of lactic acids theoretically generated per glucose residue from cellulose as a raw material. In Table 1, "-" indicates that the percentage is equal to or less than the detection limit and "trace" indicates that the percentage is less than 0.05%.

Example 2

Reaction was performed similarly to Example 1 except for using di-n-butyltin (II) trifluoromethanesulfonate $(("Bu)_2Sn(OTf)_2)$ instead of tin (II) trifluoromethanesulfonate. Various products were quantitatively analyzed by liquid chromatography. The yields of lactic acids in the analytical results are shown in Table 1 below.

Example 3

Reaction was performed similarly to Example 2 except for using pure water instead of methanol. Various products were quantitatively analyzed by liquid chromatography. The yields of lactic acids in the analytical results are shown in Table 1 below.

Comparative Example 1

Heat treatment was performed for 5 hours of reaction time using 0.1 mmol of aluminium trifluoromethanesulfonate $(Al(OTf)_3)$ instead of tin (II) trifluoromethanesulfonate. Reaction was performed under conditions similar to those of Example 1 except for the above conditions. Various products were quantitatively analyzed by liquid chromatography. The yields of lactic acids in the analytical results are shown in Table 1 below.

Comparative Example 2

Heat treatment was performed for 5 hours of reaction time using 0.1 mmol of iron trifluoromethanesulfonate $(Fe(OTf)_2)$ instead of tin (II) trifluoromethanesulfonate. Reaction was performed under conditions similar to those of Example 1 except for the above conditions. Various products were quantitatively analyzed by liquid chromatography. The yields of lactic acids in the analytical results are shown in Table 1 below.

Comparative Example 3

Heat treatment was performed for 5 hours of reaction time using 0.1 mmol of zinc trifluoromethanesulfonate $(Zn(OTf)_2)$ instead of tin (II) trifluoromethanesulfonate. Reaction was performed under conditions similar to those of Example 1 except for the above conditions. Various products were quantitatively analyzed by liquid chromatography. The yields of lactic acids in the analytical results are shown in Table 1 below.

Comparative Example 4

Heat treatment was performed for 5 hours of reaction time using 19 mg (0.1 mmol) of p-toluenesulfonic acid monohydrate $(PTSA.H_2O)$ instead of tin (II) trifluoromethanesulfonate (0.02 mmol). Reaction was performed under conditions similar to those of Example 1 except for the above conditions. Various products were quantitatively analyzed by liquid chromatography. The yields of lactic acids in the analytical results are shown in Table 1 below.

Comparative Example 5

Reaction was performed similarly to Example 1 except for using tin (II) chloride $(SnCl_2)$ instead of tin (II) trifluoromethanesulfonate. Various products were quantitatively analyzed by liquid chromatography. The yields of lactic acids in the analytical results are shown in Table 1 below.

Comparative Example 6

Reaction was performed similarly to Example 1 except for using di-n-butyltin (II) chloride $(("Bu)_2SnCl_2)$ instead of tin (II) trifluoromethanesulfonate. Various products were quantitatively analyzed by liquid chromatography. The yields of lactic acids in the analytical results are shown in Table 1 below.

Comparative Example 7

Reaction was performed similarly to Example 1 except for using di-n-butyltin (II) oxide $(("Bu)_2SnO)$ instead of tin (II)

trifluoromethanesulfonate. Various products were quantitatively analyzed by liquid chromatography. The yields of lactic acids in the analytical results are shown in Table 1 below.

Comparative Example 8

Reaction was performed similarly to Example 1 except for using di-n-butyltin (II) acetate (("Bu)$_2$Sn(OAc)$_2$) instead of tin (II) trifluoromethanesulfonate. Various products were quantitatively analyzed by liquid chromatography. The yields of lactic acids in the analytical results are shown in Table 1 below.

(Results)

As shown in Table 1, lactic acid and lactic acid ester (lactic acids) could be obtained in high yields as a result of using Sn(OTf)$_2$ (that is, tin trifluoromethanesulfonate), and ("Bu)$_2$Sn(OTf)$_2$ (that is, di-n-butyltin trifluoromethanesulfonate) as a catalyst. Also, lactic acid could be obtained in a high yield through reaction in water (Example 3).

On the other hand, very small amounts of lactic acids were generated in the case of using trifluoromethanesulfonate of a metal other than tin or organic tin (Comparative examples 1-3).

Also, in the case of using p-toluenesulfonic acid-monohydrate (PTSA.H$_2$O) as an acid catalyst (Comparative example 4), although each catalyst was used in an amount 5 times that used in Examples 1-3, the yield of lactic acid(s) was only 0.8%. This is 1/32 (or less) the yield obtained in Example 1, for example.

Furthermore, in the case of using tin (II) chloride or di-n-butyltin (II) chloride, which is not trifluoromethane sulfonate but is chloride, no lactic acids were generated. Similarly, in the case of using di-n-butyltin (II) oxide or di-n-butyltin (II) acetate, lactic acids were generated in very small amounts (Comparative examples 5-8).

left to cool at room temperature. The reaction solution was removed from the autoclave after cooling to room temperature, and various products in the solution were quantitatively analyzed by liquid chromatography in a manner similar to that in Example 1.

As a result, methyl lactate was obtained with a yield of 19.0% and lactic acid was obtained with a yield of 2.3% (total yield: 21.3%). It was thus demonstrated that lactic acid and lactic acid ester can be obtained in high yields by this method even in the case of using 2 types of tin/organic tin trifluoromethanesulfonate as catalysts.

Example 5

Cellulose (0.405 g) (corresponding to 2.5 mmol of glucose residue) that had been dried for 2 or more hours in air at 120° C., 8 mg (0.02 mmol) of tin (II) trifluoromethanesulfonate (catalyst A), 15 mg (0.08 mmol) of tin (II) chloride (SnCl$_2$) (catalyst B), 20 mL of methanol, and a stirring bar were added to a 50-mL stainless-steel autoclave (Nitto Koatsu Co. Ltd.), and then the lid was closed. Air in the autoclave was purged with nitrogen gas. After pressurization to 0.5 MPa, the interior of the autoclave was heated to 190° C. using a mantle heater while stirring the mixture with a magnetic stirrer. Subsequently, stirring was continued for 10 hours while maintaining a temperature of 190° C., heating was then stopped, and then the autoclave was left to cool at room temperature. The reaction solution was removed from the autoclave after cooling to room temperature, and various products in the solution were quantitatively analyzed by liquid chromatography in a manner similar to that in Example 1. The yields of lactic acids in the analytical results are shown in Table 2 below. In Table 2, "trace" indicates that the percentage is less than 0.05%.

TABLE 1

| | Catalyst | Amount of catalyst (mmol) | Solvent | Reaction time (h) | Methyl lactate | Lactic acid | Total | Methyl levulinate |
|---|---|---|---|---|---|---|---|---|
| Example 1 | Sn(OTf)$_2$ | 0.02 | Methanol | 10 | 14.3 | 11.7 | 26.0 | 22.4 |
| Example 2 | ("Bu)$_2$Sn(OTf)$_2$ | 0.02 | Methanol | 10 | 28.8 | 6.0 | 34.8 | 22.4 |
| Example 3 | ("Bu)$_2$Sn(OTf)$_2$ | 0.02 | Water | 10 | — | 15.7 | 15.7 | 0.9 (Levulinic acid) |
| Comparative example 1 | Al(OTf)$_3$ | 0.1 | Methanol | 5 | 1.4 | trace | 1.4 | 60.6 |
| Comparative example 2 | Fe(OTf)$_2$ | 0.1 | Methanol | 5 | 0.4 | 0.8 | 1.2 | 0.6 |
| Comparative example 3 | Zn(OTf)$_2$ | 0.1 | Methanol | 5 | 2.0 | 1.8 | 3.8 | 1.9 |
| Comparative example 4 | PTSA•H$_2$O | 0.1 | Methanol | 5 | 0.4 | 0.4 | 0.8 | 49.1 |
| Comparative example 5 | SnCl$_2$ | 0.02 | Methanol | 10 | — | — | — | 0.4 |
| Comparative example 6 | ("Bu)$_2$SnCl$_2$ | 0.02 | Methanol | 10 | — | — | — | 0.9 |
| Comparative example 7 | ("Bu)$_2$SnO | 0.02 | Methanol | 10 | 0.4 | 0.9 | 1.3 | — |
| Comparative example 8 | ("Bu)$_2$Sn(OAc)$_2$ | 0.02 | Methanol | 10 | 0.4 | 0.3 | 0.7 | 0.5 |

Example 4

Cellulose (0.405 g) (corresponding to 2.5 mmol of glucose residue) that had been dried for 2 or more hours in air at 120° C., 8 mg (0.02 mmol) of tin (II) trifluoromethanesulfonate, 11 mg (0.02 mmol) of di-n-butyltin (II) trifluoromethanesulfonate, 20 mL of methanol, and a stirring bar were added to a 50-mL stainless-steel autoclave, and then the lid was closed. Air in the autoclave was purged with nitrogen gas. After pressurization to 0.5 MPa, the interior of the autoclave was heated to 190° C. using a mantle heater while stirring the mixture with a magnetic stirrer. Subsequently, stirring was continued for 10 hours while maintaining a temperature of 190° C., heating was then stopped, and then the autoclave was Example 6

Reaction was performed similarly to Example 5 except for using 24 mg (0.08 mmol) of di-n-butyltin chloride (("Bu)$_2$SnCl$_2$) instead of tin (II) chloride. Various products in the thus obtained reaction solution were quantitatively analyzed by liquid chromatography. The yields of lactic acids in the analytical results are shown in Table 2 below.

Example 7

Cellulose (0.405 g) (corresponding to 2.5 mmol of glucose residue) that had been dried for 2 or more hours in air at 120° C., 11 mg (0.02 mmol) of di-n-butyltin (II) trifluoromethanesulfonate (("Bu)$_2$Sn(OTf)$_2$) (catalyst A), 15 mg (0.08 mmol) of tin (II) chloride (SnCl$_2$) (catalyst B), 20 mL of methanol, and a stirring bar were added to a 50-mL stainless-steel autoclave, and then the lid was closed. Air in the autoclave was purged with nitrogen gas. After pressurization to 0.5 MPa, the interior of the autoclave was heated to 190° C. using a mantle heater while stirring the mixture with a magnetic stirrer. Subsequently, stirring was continued for 10 hours while maintaining a temperature of 190° C., heating was then stopped, and then the autoclave was left to cool at room temperature. The reaction solution was removed from the autoclave after cooling to room temperature, and various products in the solution were quantitatively analyzed by liquid chromatography in a manner similar to that in Example 1. The yields of lactic acids in the analytical results are shown in Table 2 below.

Example 8

Reaction was performed similarly to Example 7 except for using 43 mg (0.08 mmol) of di-n-butyltin (II) trifluoromethanesulfonate (catalyst A) and 4 mg (0.02 mmol) of tin (II) chloride (catalyst B). Various products in the thus obtained reaction solution were quantitatively analyzed by liquid chromatography. The yields of lactic acids in the analytical results are shown in Table 2 below.

Example 9

Reaction was performed similarly to Example 7 except for adding 18 mg (0.16 mmol) of catechol in addition to cellulose, di-n-butyltin (II) trifluoromethanesulfonate, tin (II) chloride, and methanol. Various products in the thus obtained reaction solution were quantitatively analyzed by liquid chromatography. The yields of lactic acids in the analytical results are shown in Table 2 below.

Example 10

Reaction was performed similarly to Example 7 except for using 24 mg (0.08 mmol) of di-n-butyltin chloride (("Bu)$_2$SnCl$_2$) instead of tin (II) chloride. Various products in the thus obtained reaction solution were quantitatively analyzed by liquid chromatography. The yields of lactic acids in the analytical results are shown in Table 2 below.

Comparative Example 9

Reaction was performed similarly to Example 6 except for using 4 mg (0.02 mmol) of p-toluenesulfonic acid monohydrate (PTSA.H$_2$O) instead of tin (II) trifluoromethanesulfonate. Various products in the thus obtained reaction solution were quantitatively analyzed by liquid chromatography. The yields of lactic acids in the analytical results are shown in Table 2 below.

(Results)

As shown in Table 2, lactic acids could be obtained in high yields even in the cases of using tin/organic tin trifluoromethanesulfonate with a tin compound other than trifluoromethanesulfonate. Higher yields were more likely to be obtained particularly in the cases of combined use with tin/organic tin chloride. On the other hand, lactic acids were almost never generated in the case (Comparative example 9) of using a tin compound other than trifluoromethanesulfonate as a catalyst.

In Examples 7 and 8 wherein the proportions of two types of catalyst were varied, the yields of lactic acids were higher in a case of a lower proportion (20%; Example 7) of di-n-butyltin (II) trifluoromethanesulfonate (catalyst A) relative to the total amount of catalysts (catalysts A+B) used than that in a case of a higher proportion (80%; Example 8) of the same. Therefore, it was demonstrated that when another tin compound is added to tin/organic tin trifluoromethanesulfonate, the relatively low proportion of tin trifluoromethanesulfonate relative to the total amount of catalysts used is useful for obtaining lactic acids in high yields.

In addition, as a result of further adding catechol for reaction, which is a phenolic compound, in Example 9, lactic acids were obtained in higher yields than in the case (Example 7) of adding no catechol.

TABLE 2

| | Catalyst A | Catalyst B | | Yield (%) | | | |
|---|---|---|---|---|---|---|---|
| | (Amount added (mmol)) | (Amount added (mmol)) | Additive (mmol) | Methyl lactate | Lactic acid | Total (Lactic acids) | Methyl levulinate |
| Example 5 | Sn(OTf)$_2$ (0.02) | SnCl$_2$ (0.08) | | 15.9 | 12.1 | 28.0 | 24.9 |
| Example 6 | Sn(OTf)$_2$ (0.02) | ("Bu)$_2$SnCl$_2$ (0.08) | | 29.9 | 6.6 | 36.5 | 12.3 |
| Example 7 | ("Bu)$_2$Sn(OTf)$_2$ (0.02) | SnCl$_2$ (0.08) | | 15.7 | 11.5 | 27.2 | 26.1 |
| Example 8 | ("Bu)$_2$Sn(OTf)$_2$ (0.08) | SnCl$_2$ (0.02) | | 24.4 | trace | 24.4 | 16.4 |
| Example 9 | ("Bu)$_2$Sn(OTf)$_2$ (0.02) | SnCl$_2$ (0.08) | Catechol (0.16) | 23.5 | 11.7 | 35.2 | 15.2 |
| Example 10 | ("Bu)$_2$Sn(OTf)$_2$ (0.02) | ("Bu)$_2$SnCl$_2$ (0.08) | | 31.3 | 5.5 | 36.8 | 13.1 |
| Comparative example 9 | PTSA•H$_2$O (0.02) | ("Bu)$_2$SnCl$_2$ (0.08) | | 0.3 | trace | 0.3 | 1.3 |

Example 11

Cellulose (0.405 g) (corresponding to 2.5 mmol of glucose residue) that had been dried for 2 or more hours in air at 120° C., 11 mg (0.02 mmol) of di-n-butyltin (II) trifluoromethanesulfonate ("Bu$_2$Sn(OTf)$_2$; Tf=CF$_3$SO$_2$) and 28 mg (0.08 mmol) of indium bromide (InBr$_3$) as catalysts, 20 mL of methanol, and a stirring bar were added to a 50-mL stainless-steel autoclave, and then the lid was closed. Air in the autoclave was purged with nitrogen gas. After pressurization to 0.5 MPa, the interior of the autoclave was heated to 190° C. using a mantle heater while stirring the mixture with a magnetic stirrer. Subsequently, stirring was continued for 10 hours while maintaining a temperature of 190° C., heating was then stopped, and then the autoclave was left to cool at room temperature. The reaction solution was removed from the autoclave after cooling to room temperature, and various products in the solution were quantitatively analyzed by liquid chromatography. The yields of lactic acids in the analytical results are shown in Table 3 below. In Table 3, "-" indicates that the percentage is equal to or less than the detection limit.

Example 12

Reaction was performed similarly to Example 11 except for adding 11 mg (0.1 mmol) of catechol in addition to cellulose, di-n-butyltin (II) trifluoromethanesulfonate, indium bromide, and methanol. Various products in the thus obtained reaction solution were quantitatively analyzed by liquid chromatography. The yields of lactic acids in the analytical results are shown in Table 3 below.

Comparative Example 10

Reaction was performed similarly to Example 11 except for using 18 mg (0.05 mmol) of indium bromide ($InBr_3$) alone as a catalyst without using di-n-butyltin (II) trifluoromethanesulfonate. Various products in the thus obtained reaction solution were quantitatively analyzed by liquid chromatography. The yields of lactic acids in the analytical results are shown in Table 3 below.

(Results)

As shown in Table 3, through the use of organic tin trifluoromethanesulfonate in combination with indium bromide, lactic acids could be obtained in higher yields than in the case (the above Example 2 (Table 1)) of using organic tin trifluoromethanesulfonate alone. Therefore, it was demonstrated that the use of tin/organic tin trifluoromethanesulfonate in combination with an indium compound is useful for obtaining lactic acids in high yields.

In addition, as a result of performing a reaction with the further addition of catechol, which is a phenolic compound, in Example 12, lactic acids could be obtained in higher yields than in the case of adding no catechol (Example 11).

solution was removed from the autoclave after cooling to room temperature, and various products in the solution were quantitatively analyzed by liquid chromatography. The yields of lactic acids in the analytical results are shown in Table 4 below. In Table 4, "-" indicates that the percentage is equal to or less than the detection limit.

Example 14

Reaction was performed similarly to Example 13 except for using 42 mg (0.1 mmol) of tin (II) trifluoromethanesulfonate ($Sn(OTf)_2$; $Tf=CF_3SO_2$) and 33 mg (0.05 mmol) of rhenium carbonyl ($Re_2(CO)_{10}$) as catalysts. Various products in the thus obtained reaction solution were quantitatively analyzed by liquid chromatography. The yields of lactic acids in the analytical results are shown in Table 4 below.

Example 15

Heat treatment was performed for 24 hours of reaction time at 200° C. using 64 mg (0.12 mmol) of di-n-butyltin (II) trifluoromethanesulfonate (($"Bu$)$_2Sn(OTf)_2$) and 20 mg (0.1 mmol) of manganese chloride tetrahydrate ($MnCl_2.4H_2O$) as catalysts. Reaction was performed under conditions similar to those of Example 13 except for the above conditions. Various products in the thus obtained reaction solution were quantitatively analyzed by liquid chromatography. The yields of lactic acids in the analytical results are shown in Table 4 below.

Example 16

Heat treatment was performed for 24 hours of reaction time at 200° C. using 32 mg (0.06 mmol) of di-n-butyltin (II) trifluoromethanesulfonate (($"Bu$)$_2Sn(OTf)_2$), 10 mg (0.05 mmol) of manganese chloride tetrahydrate ($MnCl_2.4H_2O$), and 16 mg (0.025 mmol) of rhenium carbonyl ($Re_2(CO)_{10}$) as catalysts. Reaction was performed under conditions similar to those of Example 13 except for the above conditions. Various products in the thus obtained reaction solution were

TABLE 3

| | | | | | Yield/% | | | |
|---|---|---|---|---|---|---|---|---|
| | Catalyst/mmol | | Additive/mmol | Temperature/ °C. | Time/ h | Methyl lactate | Lactic acid | Total (Lactic acids) | Methyl levulinate |
| Example 11 | "Bu$_2$Sn(OTf)$_2$/0.02 | InBr$_3$/0.08 | | 190 | 10 | 30.6 | 6.1 | 36.7 | 24.1 |
| Example 12 | "Bu$_2$Sn(OTf)$_2$/0.02 | InBr$_3$/0.08 | Catechol/0.1 | 190 | 10 | 32.0 | 7.9 | 39.9 | 24.4 |
| Comparative example 10 | | InBr$_3$/0.05 | | 180 | 10 | — | — | — | — |

Example 13

Cellulose (0.405 g) (corresponding to 2.5 mmol of glucose residue) that had been dried for 2 or more hours in air at 120° C., 53 mg (0.1 mmol) of di-n-butyltin (II) trifluoromethanesulfonate (($"Bu$)$_2Sn(OTf)_2$), 33 mg (0.05 mmol) of rhenium carbonyl ($Re_2(CO)_{10}$), 20 mL of methanol, and a stirring bar were added to a 50-mL stainless-steel autoclave, and then the lid was closed. Air in the autoclave was purged with nitrogen gas. After pressurization to 0.5 MPa, the interior of the autoclave was heated to 190° C. using an electric furnace while stirring the mixture with a magnetic stirrer. Subsequently, stirring was continued for 10 hours while maintaining a temperature of 190° C., heating was then stopped, and then the autoclave was left to cool at room temperature. The reaction quantitatively analyzed by liquid chromatography. The yields of lactic acids in the analytical results are shown in Table 4 below.

Example 17

Heat treatment was performed for 24 hours of reaction time at 200° C. using 64 mg (0.12 mmol) of di-n-butyltin (II) trifluoromethanesulfonate (($"Bu$)$_2Sn(OTf)_2$), 20 mg (0.1 mmol) of manganese chloride tetrahydrate ($MnCl_2.4H_2O$), and 33 mg (0.05 mmol) of rhenium carbonyl ($Re_2(CO)_{10}$) as catalysts. Reaction was performed under conditions similar to those of Example 13 except for the above conditions. Various products in the thus obtained reaction solution were quantitatively analyzed by liquid chromatography. The yields of lactic acids in the analytical results are shown in Table 4 below.

Example 18

Heat treatment was performed for 62 hours of reaction time at 200° C. using 32 mg (0.06 mmol) of di-n-butyltin (II) trifluoromethanesulfonate ((″Bu)$_2$Sn(OTf)$_2$), 10 mg (0.05 mmol) of magnesium chloride hexahydrate (MgCl$_2$.6H$_2$O), and 16 mg (0.025 mmol) of rhenium carbonyl (Re$_2$(CO)$_{10}$) as catalysts. Reaction was performed under conditions similar to those of Example 13 except for the above conditions. Various products in the thus obtained reaction solution were quantitatively analyzed by liquid chromatography. The yields of lactic acids in the analytical results are shown in Table 4 below.

Example 19

Heat treatment was performed for 10 hours of reaction time at 200° C. using 50 mg (0.12 mmol) of tin (II) trifluoromethanesulfonate (Sn(OTf)$_2$; Tf=CF$_3$SO$_2$), 20 mg (0.1 mmol) of magnesium chloride hexahydrate (MgCl$_2$.6H$_2$O), and 33 mg (0.05 mmol) of rhenium carbonyl (Re$_2$(CO)$_{10}$) as catalysts. Reaction was performed under conditions similar to those of Example 13 except for the above conditions. Various products in the thus obtained reaction solution were quantitatively analyzed by liquid chromatography. The yields of lactic acids in the analytical results are shown in Table 4 below.

(Results)

As shown in Table 4, as a result of using Sn(OTf)$_2$ that is tin trifluoromethanesulfonate or (″Bu)$_2$Sn(OTf)$_2$ that is di-n-butyltin trifluoromethanesulfonate in combination with rhenium carbonyl (Re$_2$(CO)$_{10}$) and/or manganese chloride tetrahydrate (MnCl$_2$.4H$_2$O) or magnesium chloride hexahydrate (MgCl$_2$.6H$_2$O) as a catalyst, lactic acids, and particularly lactic acid ester was obtained with a yield higher than those in the case (the above Examples 1 and 2 (Table 1)) of using Sn(OTf)$_2$ or (″Bu)$_2$Sn(OTf)$_2$ alone. However, unlike Examples 1 and 2, no lactic acid was generated.

Furthermore, lactic acids and particularly lactic acid ester could be obtained in a high yield in the case of using Sn(OTf)$_2$ or (″Bu)$_2$Sn(OTf)$_2$ that is di-n-butyltin trifluoromethanesulfonate, rhenium carbonyl (Re$_2$(CO)$_{10}$) and manganese chloride tetrahydrate (MnCl$_2$.4H$_2$O) or magnesium chloride hexahydrate (MgCl$_2$.6H$_2$O) in combination as a catalyst (Examples 16-19), compared with the cases (Examples 13-15) of using two types of catalyst, Sn(OTf)$_2$ or (″Bu)$_2$Sn(OTf)$_2$ that is di-n-butyltin trifluoromethanesulfonate and rhenium carbonyl (Re$_2$(CO)$_{10}$) or manganese chloride tetrahydrate (MnCl$_2$.4H$_2$O) or magnesium chloride hexahydrate (MgCl$_2$.6H$_2$O). Therefore, it was demonstrated that the combined use of tin/organic tin trifluoromethanesulfonate with a rhenium compound and a manganese compound or a magnesium compound is useful for obtaining lactic acids in high yields.

TABLE 4

| | Catalyst/mmol | | | Temperature/ °C. | Time/ h | Methyl lactate | Lactic acid | Total (Lactic acids) | Methyl levulinate |
|---|---|---|---|---|---|---|---|---|---|
| Example 13 | ″Bu$_2$Sn(OTf)$_2$/0.1 | | Re$_2$(CO)$_{10}$/0.05 | 190 | 10 | 27.9 | — | 27.9 | 14.3 |
| Example 14 | Sn(OTf)$_2$/0.1 | | Re$_2$(CO)$_{10}$/0.05 | 190 | 10 | 16.4 | — | 16.4 | 32.0 |
| Example 15 | ″Bu$_2$Sn(OTf)$_2$/0.12 | MnCl$_2$•4H$_2$O/0.1 | | 200 | 24 | 31.9 | — | 31.9 | 9.5 |
| Example 16 | ″Bu$_2$Sn(OTf)$_2$/0.06 | MnCl$_2$•4H$_2$O/0.05 | Re$_2$(CO)$_{10}$/0.025 | 200 | 24 | 46.4 | — | 46.4 | 2.6 |
| Example 17 | ″Bu$_2$Sn(OTf)$_2$/0.12 | MnCl$_2$•4H$_2$O/0.1 | Re$_2$(CO)$_{10}$/0.05 | 200 | 24 | 42.2 | — | 42.2 | 6.5 |
| Example 18 | ″Bu$_2$Sn(OTf)$_2$/0.06 | MgCl$_2$•6H$_2$O/0.05 | Re$_2$(CO)$_{10}$/0.025 | 200 | 62 | 44.4 | — | 44.4 | 4.2 |
| Example 19 | Sn(OTf)$_2$/0.12 | MgCl$_2$•6H$_2$O/0.1 | Re$_2$(CO)$_{10}$/0.05 | 200 | 10 | 38.6 | — | 38.6 | 9.6 |

Example 20

D-fructose (0.45 g (2.5 mmol)) as a raw material, 5 mg (0.025 mmol) of tin (II) chloride as a catalyst, 20 mg (0.1 mmol) of manganese chloride tetrahydrate as a promoter, 10 mL of methanol as a solvent, and a stirring bar were added to a 50-mL stainless-steel autoclave (Taiatsu Techno Corporation), and then the lid was closed. Air in the autoclave was purged with nitrogen gas. After pressurization to 0.5 MPa, the autoclave was heated to 150° C. using an electric furnace while stirring the mixture with a magnetic stirrer. Subsequently, stirring was continued for 5 hours while maintaining a temperature of 150° C., and then the autoclave was left to cool at room temperature. The reaction solution was removed from the autoclave after cooling, and products in the solution were quantitatively analyzed by liquid chromatography. The yields of lactic acids in the analytical results are shown in Table 5 below. Each yield is represented in percentage (%) figures for the number of moles (mol) of a product with respect to the number of moles (lactic acids/fructose=5 mmol/2.5 mmol) of lactic acids theoretically generated from D-fructose as a raw material. In Table, "trace" indicates that the percentage is less than 0.5%.

Example 21

Reaction was performed similarly to Example 20 except for using 7 mg (0.025 mmol) of tin (II) bromide instead of tin (II) chloride. Various products were quantitatively analyzed by liquid chromatography. The yields of lactic acids in the analytical results are shown in Table 5 below.

Example 22

Reaction was performed similarly to Example 20 except for using 28 mg (0.1 mmol) of n-butyltin trichloride instead of tin (II) chloride. Various products were quantitatively analyzed by liquid chromatography. The yields of lactic acids in the analytical results are shown in Table 5 below.

Example 23

Heat treatment was performed for 10 hours of reaction time using 30 mg (0.1 mmol) of phenyltin trichloride instead of tin (II) chloride. Reaction was performed under conditions similar to those of Example 20 except for the above conditions. Various products were quantitatively analyzed by liquid chromatography. The yields of lactic acids in the analytical results are shown in Table 5 below.

Example 24

Tin trifluoromethanesulfonate (42 mg (0.1 mmol)) was used instead of tin (II) chloride and 20 mg (0.1 mmol) of magnesium chloride hexahydrate was used instead of manganese chloride tetrahydrate. Reaction was performed under conditions similar to those of Example 20 except for the above conditions. Various products were quantitatively analyzed by liquid chromatography. The yields of lactic acids in the analytical results are shown in Table 5 below.

Example 25

Reaction was performed similarly to Example 20 except for using 8 mg (0.02 mmol) of tin trifluoromethanesulfonate and 23 mg (0.08 mmol) of n-butyltin trichloride instead of tin (II) chloride. Various products were quantitatively analyzed by liquid chromatography. The yields of lactic acids in the analytical results are shown in Table 5 below.

Comparative Example 11

Reaction was performed similarly to Example 20 except for using 24 mg (0.125 mmol) of tin (II) chloride as a catalyst without using a promoter. Various products were quantitatively analyzed by liquid chromatography. The yields of lactic acids in the analytical results are shown in Table 5 below.

Comparative Example 12

Reaction was performed similarly to Example 20 except for using 35 mg (0.125 mmol) of tin (II) bromide as a catalyst without using a promoter. Various products were quantitatively analyzed by liquid chromatography. The yields of lactic acids in the analytical results are shown in Table 5 below.

Comparative Example 13

Heat treatment was performed for 10 hours of reaction time using 35 mg (0.1 mmol) of tin (IV) chloride pentahydrate as a catalyst without using a promoter. Reaction was performed under conditions similar to those of Example 20 except for the above conditions. Various products were quantitatively analyzed by liquid chromatography. The yields of lactic acids in the analytical results are shown in Table 5 below.

Comparative Example 14

Heat treatment was performed for at 160° C. using 21 mg (0.05 mmol) of tin trifluoromethanesulfonate as a catalyst without using a promoter. Reaction was performed under conditions similar to those of Example 20 except for the above conditions. Various products were quantitatively analyzed by liquid chromatography. The yields of lactic acids in the analytical results are shown in Table 5 below.

Comparative Example 15

Reaction was performed similarly to Example 20 except for using 20 mg (0.1 mmol) of manganese chloride tetrahydrate as a promoter without using a catalyst. Various products were quantitatively analyzed by liquid chromatography. The yields of lactic acids in the analytical results are shown in Table 5 below.

Comparative Example 16

Reaction was performed similarly to Example 20 except for using 20 mg (0.1 mmol) of magnesium chloride hexahydrate as a promoter without using a catalyst. Various products were quantitatively analyzed by liquid chromatography. The yields of lactic acids in the analytical results are shown in Table 5 below.

Example 26

Heat treatment was performed at 160° C. using 6 mg (0.025 mmol) of cobalt chloride hexahydrate instead of manganese chloride tetrahydrate. Reaction was performed under conditions similar to those of Example 20 except for the above conditions. Various products were quantitatively analyzed by liquid chromatography. The yields of lactic acids in the analytical results are shown in Table 5 below.

Example 27

Heat treatment was performed at 160° C. using 9 mg (0.05 mmol) of tin (II) chloride as a catalyst and 12 mg (0.05 mmol) of cobalt chloride hexahydrate as a promoter. Reaction was performed under conditions similar to those of Example 20 except for the above conditions. Various products were quantitatively analyzed by liquid chromatography. The yields of lactic acids in the analytical results are shown in Table 5 below.

Example 28

Heat treatment was performed at 160° C. using 6 mg (0.025 mmol) of nickel chloride hexahydrate instead of manganese chloride tetrahydrate. Reaction was performed under conditions similar to those of Example 20 except for the above conditions. Various products were quantitatively analyzed by liquid chromatography. The yields of lactic acids in the analytical results are shown in Table 5 below.

Example 29

Heat treatment was performed at 160° C. using 9 mg (0.05 mmol) of tin (II) chloride as a catalyst and 12 mg (0.05 mmol) of nickel chloride hexahydrate as a promoter. Reaction was performed under conditions similar to those of Example 20 except for the above conditions. Various products were quantitatively analyzed by liquid chromatography. The yields of lactic acids in the analytical results are shown in Table 5 below.

Comparative Example 17

Heat treatment was performed at 160° C. using 5 mg (0.025 mmol) of tin (II) chloride as a catalyst without using a promoter. Reaction was performed under conditions similar to those of Example except for the above conditions. Various products were quantitatively analyzed by liquid chromatography. The yields of lactic acids in the analytical results are shown in Table 5 below.

Comparative Example 18

Heat treatment was performed at 160° C. using 9 mg (0.05 mmol) of tin (II) chloride as a catalyst without using a promoter. Reaction was performed under conditions similar to those of Example except for the above conditions. Various products were quantitatively analyzed by liquid chromatography. The yields of lactic acids in the analytical results are shown in Table 5 below.

Comparative Example 19

Heat treatment was performed at 160° C. using 24 mg (0.1 mmol) of cobalt chloride hexahydrate as a promoter without using a catalyst. Reaction was performed under conditions similar to those of Example 20 except for the above conditions. Various products were quantitatively analyzed by liquid chromatography. The yields of lactic acids in the analytical results are shown in Table 5 below.

Comparative Example 20

Reaction was performed similarly to Example 20 except for using 24 mg (0.1 mmol) of nickel chloride hexahydrate as a promoter without using a catalyst. Various products were quantitatively analyzed by liquid chromatography. The yields of lactic acids in the analytical results are shown in Table 5 below.

Example 30

Reaction was performed similarly to Example 20 except for using 4 mg (0.1 mmol) of lithium chloride instead of manganese chloride tetrahydrate. Various products were quantitatively analyzed by liquid chromatography. The yields of lactic acids in the analytical results are shown in Table 5 below.

Example 31

Reaction was performed similarly to Example 20 except for using 20 mg (0.1 mmol) of iron (II) chloride tetrahydrate instead of manganese chloride tetrahydrate. Various products were quantitatively analyzed by liquid chromatography. The yields of lactic acids in the analytical results are shown in Table 5 below.

Comparative Example 21

4 mg (0.1 mmol) of lithium chloride was used as a promoter but no catalyst was used. Reaction was performed under conditions similar to those of Example 20 except for the above conditions. Various products were quantitatively analyzed by liquid chromatography. The yields of lactic acids in the analytical results are shown in Table 5 below.

Comparative Example 22

Iron (II) chloride tetrahydrate (20 mg (0.1 mmol)) was used as a promoter but no catalyst was used. Reaction was performed under conditions similar to those of Example 20 except for the above conditions. Various products were quantitatively analyzed by liquid chromatography. The yields of lactic acids in the analytical results are shown in Table 5 below.

(Results)

As shown in Table 5, lactic acid ester could be obtained in a higher yield in the cases (Examples 20-31) of using a tin-containing compound in combination with a promoter, compared with the cases (Comparative examples 11-22) of not using a tin-containing compound or a promoter. Lactic acid ester was likely obtained in a higher yield in the cases (Examples 20-25) of using manganese chloride tetrahydrate or magnesium chloride hexahydrate as a promoter. Also, particularly a high yield was obtained when two types of tin-containing compound were used in combination with a promoter (Example 25). Furthermore, regarding Examples 26 and 27 and Examples 28 and 29 wherein the ratio of two types of catalyst was varied, the yield of lactic acid ester was higher in the cases (Examples 27 and 29) of using a higher total amount of a tin-containing compound and a promoter than in the cases (Examples 26 and 28) of using the same in a lower amount. Therefore, it was demonstrated that the relatively high total amount of a tin-containing compound and a promoter is useful for obtaining lactic acid ester in a high yield.

TABLE 5

|  |  |  |  |  | Yield/% | |
|---|---|---|---|---|---|---|
|  | Tin-containing compound (catalyst) (mmol) | Promoter (mmol) | Temperature/ °C. | Time/ h | Methyl lactate | Methyl levulinate |
| Example 20 | $SnCl_2$ (0.025) | $MnCl_2 \cdot 4H_2O$ (0.1) | 150 | 5 | 59 | 1 |
| Example 21 | $SnBr_2$ (0.025) | $MnCl_2 \cdot 4H_2O$ (0.1) | 150 | 5 | 49 | 1 |
| Example 22 | $^nBuSnCl_3$ (0.1) | $MnCl_2 \cdot 4H_2O$ (0.1) | 150 | 5 | 60 | 3 |
| Example 23 | $PhSnCl_3$ (0.1) | $MnCl_2 \cdot 4H_2O$ (0.1) | 150 | 10 | 55 | trace |
| Example 24 | $Sn(OTf)_2$ (0.1) | $MgCl_2 \cdot 6H_2O$ (0.1) | 150 | 5 | 56 | 2 |
| Example 25 | $Sn(OTf)_2$ (0.02) + $^nBuSnCl_3$ (0.08) | $MnCl_2 \cdot 4H_2O$ (0.1) | 150 | 5 | 61 | 3 |
| Comparative example 11 | $SnCl_2$ (0.125) |  | 150 | 5 | 48 | 11 |
| Comparative example 12 | $SnBr_2$ (0.125) |  | 150 | 5 | 34 | 19 |
| Comparative example 13 | $SnCl_4 \cdot 5H_2O$ (0.1) |  | 150 | 10 | 40 | 7 |
| Comparative example 14 | $Sn(OTf)_2$ (0.05) |  | 160 | 5 | 14 | 52 |
| Comparative example 15 |  | $MnCl_2 \cdot 4H_2O$ (0.1) | 150 | 5 | 4 | trace |
| Comparative example 16 |  | $MgCl_2 \cdot 6H_2O$ (0.1) | 150 | 5 | 13 | 1 |
| Example 26 | $SnCl_2$ (0.025) | $CoCl_2 \cdot 6H_2O$ (0.025) | 160 | 5 | 49 | 1 |
| Example 27 | $SnCl_2$ (0.05) | $CoCl_2 \cdot 6H_2O$ (0.05) | 160 | 5 | 51 | 2 |
| Example 28 | $SnCl_2$ (0.025) | $NiCl_2 \cdot 6H_2O$ (0.025) | 160 | 5 | 51 | 1 |
| Example 29 | $SnCl_2$ (0.05) | $NiCl_2 \cdot 6H_2O$ (0.05) | 160 | 5 | 54 | 1 |
| Comparative example 17 | $SnCl_2$ (0.025) |  | 160 | 5 | 39 | 4 |
| Comparative example 18 | $SnCl_2$ (0.05) |  | 160 | 5 | 44 | 6 |

TABLE 5-continued

|  | Tin catalyst (mmol) | Promoter (mmol) | Temperature/ °C. | Time/ h | Yield/% Methyl lactate | Methyl levulinate |
|---|---|---|---|---|---|---|
| Comparative example 19 |  | $CoCl_2 \cdot 6H_2O$ (0.1) | 160 | 5 | 20 | 2 |
| Comparative example 20 |  | $NiCl_2 \cdot 6H_2O$ (0.1) | 150 | 5 | 11 | 1 |
| Example 30 | $SnCl_2$ (0.025) | LiCl (0.1) | 150 | 5 | 45 | 1 |
| Example 31 | $SnCl_2$ (0.025) | $FeCl_2 \cdot 4H_2O$ (0.1) | 150 | 5 | 46 | 1 |
| Comparative example 21 |  | LiCl (0.1) | 150 | 5 | 1 | trace |
| Comparative example 22 |  | $FeCl_2 \cdot 4H_2O$ (0.1) | 150 | 5 | 7 | trace |

Example 32

D-fructose (0.45 g (2.5 mmol)) as a raw material, 35 mg (0.1 mmol) of tin (IV) chloride pentahydrate as a catalyst, 57 mg (0.1 mmol) of bis(triphenylphosphine)iminium chloride as a promoter, 20 mL of methanol as a solvent, and a stirring bar were added to a 50-mL stainless-steel autoclave (Taiatsu Techno Corporation), and then the lid was closed. Air in the autoclave was purged with nitrogen gas. After pressurization to 0.5 MPa, the autoclave was heated to 150° C. using an electric furnace while stirring the mixture with a magnetic stirrer. Subsequently, stirring was continued for 10 hours while maintaining a temperature of 150° C., and then the autoclave was left to cool at room temperature. The reaction solution was removed from the autoclave after cooling, and products in the solution were quantitatively analyzed by liquid chromatography. The yields of lactic acids in the analytical results are shown in Table 6 below. Each yield is represented in percentage (%) figures for the number of moles (mol) of each product with respect to the number of moles (lactic acids/fructose=5 mmol/2.5 mmol) of lactic acids theoretically generated from D-fructose as a raw material.

Example 33

Reaction was performed similarly to Example 32 except for using 115 mg (0.2 mmol) of bis(triphenylphosphine)iminium chloride as a promoter. Various products were quantitatively analyzed by liquid chromatography. The yields of lactic acids in the analytical results are shown in Table 6 below.

Example 34

Reaction was performed similarly to Example 32 except for using 30 mg (0.1 mmol) of phenyltin trichloride instead of tin (IV) chloride pentahydrate. Various products were quantitatively analyzed by liquid chromatography. The yields of lactic acids in the analytical results are shown in Table 6 below.

Example 35

Reaction was performed similarly to Example 32 except for using 40 mg (0.1 mmol) of trioctylmethylammonium chloride as a promoter. Various products were quantitatively analyzed by liquid chromatography. The yields of lactic acids in the analytical results are shown in Table 6 below.

Example 36

Reaction was performed similarly to Example 32 except for using 28 mg (0.1 mmol) of tetrabutylammonium bromide as a promoter. Various products were quantitatively analyzed by liquid chromatography. The yields of lactic acids in the analytical results are shown in Table 6 below.

Comparative Example 23

Reaction was performed similarly to Example 32 except for using 35 mg (0.1 mmol) of tin (IV) chloride pentahydrate as a catalyst without using a promoter. Various products were quantitatively analyzed by liquid chromatography. The yields of lactic acids in the analytical results are shown in Table 6 below.

(Results)

As shown in Table 6, lactic acids could be obtained in high yields in the cases (Examples 32-36) of using tin/organic tin chloride with a quaternary ammonium salt, compared with the case (Comparative example 13) of using no quaternary ammonium salt. Also, lactic acids could be obtained in higher yields in the case (Example 34) of using organic tin chloride, compared with the case (Example 32) of using tin chloride.

TABLE 6

|  | Tin-containing compound (catalyst) (mmol) | Promoter (mmol) | Temperature/ °C. | Time/ h | Yield/% Methyl lactate | Methyl levulinate |
|---|---|---|---|---|---|---|
| Example 32 | $SnCl_4 \cdot 5H_2O$ (0.1) | $[PPN]^+Cl^-$ (0.1) | 150 | 10 | 52 | 3 |
| Example 33 | $SnCl_4 \cdot 5H_2O$ (0.1) | $[PPN]^+Cl^-$ (0.2) | 150 | 10 | 53 | 2 |
| Example 34 | $PhSnCl_3$ (0.1) | $[PPN]^+Cl^-$ (0.1) | 150 | 10 | 58 | 2 |
| Example 35 | $SnCl_4 \cdot 5H_2O$ (0.1) | $[Oct_3MeN]^+Cl^-$ (0.1) | 150 | 10 | 52 | 2 |

TABLE 6-continued

| | Tin-containing compound (catalyst) (mmol) | Promoter (mmol) | Temperature/ °C. | Time/ h | Yield/% Methyl lactate | Methyl levulinate |
|---|---|---|---|---|---|---|
| Example 36 | SnCl$_4$•5H$_2$O (0.1) | [Bu$_4$N]$^+$Br$^-$ (0.1) | 150 | 10 | 50 | 3 |
| Comparative example 23 | SnCl$_4$•5H$_2$O (0.1) | | 150 | 10 | 40 | 7 |

(2) Method Using a Rhenium Compound as a Catalyst

Example 37

D-fructose (0.45 g (2.5 mmol)) as a raw material, 130.6 mg (0.2 mmol) of rhenium carbonyl as a catalyst, 20 mL of methanol as a solvent, and a stirring bar were added to a 50-mL stainless-steel autoclave (Taiatsu Techno Corporation), and then the lid was closed. Air in the autoclave was purged with nitrogen gas. After pressurization to 0.5 MPa, the autoclave was heated to 150° C. using an electric furnace while stirring the mixture with a magnetic stirrer. Subsequently, stirring was continued for 10 hours while maintaining a temperature of 150° C., and then the autoclave was left to cool at room temperature. The reaction solution was removed from the autoclave after cooling, and products in the solution were quantitatively analyzed by liquid chromatography. The yields of lactic acids in the analytical results are shown in Table 7 below. Each yield is represented in percentage (%) figures for the number of moles (mol) of each product with respect to the number of moles (lactic acids/fructose=5 mmol/2.5 mmol) of lactic acids theoretically generated from D-fructose as a raw material. In Table 7, "trace" indicates that the percentage is less than 0.5%.

Example 38

Reaction was performed similarly to Example 37 except for adding 65.3 mg (0.1 mmol) of rhenium carbonyl and further adding 20.3 mg (0.1 mmol) of magnesium chloride hexahydrate as catalysts. Various products in the thus obtained reaction solution were quantitatively analyzed by liquid chromatography. The yields of lactic acids in the analytical results are shown in Table 7 below.

Example 39

Reaction was performed similarly to Example 37 except for using 65.3 mg (0.1 mmol) of rhenium carbonyl and 19.8 mg (0.1 mmol) of manganese chloride tetrahydrate as catalysts. Various products were quantitatively analyzed by liquid chromatography. The yields of lactic acids in the analytical results are shown in Table 7 below.

Example 40

Reaction was performed similarly to Example 37 except for using 65.3 mg (0.1 mmol) of rhenium carbonyl and 19.9 mg (0.1 mmol) of iron chloride hexahydrate as catalysts. Various products were quantitatively analyzed by liquid chromatography. The yields of lactic acids in the analytical results are shown in Table 7 below.

Example 41

Reaction was performed similarly to Example 37 except for using 65.3 mg (0.1 mmol) of rhenium carbonyl and 23.8 mg (0.1 mmol) of cobalt chloride hexahydrate as catalysts. Various products were quantitatively analyzed by liquid chromatography. The yields of lactic acids in the analytical results are shown in Table 7 below.

Example 42

Reaction was performed similarly to Example 37 except for using 65.3 mg (0.1 mmol) of rhenium carbonyl and 23.8 mg (0.1 mmol) of nickel chloride tetrahydrate as catalysts. Various products were quantitatively analyzed by liquid chromatography. The yields of lactic acids in the analytical results are shown in Table 7 below.

Example 43

Reaction was performed similarly to Example 37 except for using 65.3 mg (0.1 mmol) of rhenium carbonyl and 19 mg (0.1 mmol) of tin (II) chloride as catalysts. Various products were quantitatively analyzed by liquid chromatography. The yields of lactic acids in the analytical results are shown in Table 7 below.

Comparative Example 24

Reaction was performed similarly to Example 37 except for using 39.6 mg (0.2 mmol) of manganese chloride tetrahydrate alone as a catalyst. Various products were quantitatively analyzed by liquid chromatography. The yields of lactic acids in the analytical results are shown in Table 7 below.

Example 44

Reaction was performed similarly to Example 37 except for using 16.3 mg (0.025 mmol) of rhenium carbonyl and further using 19.8 mg (0.1 mmol) of manganese chloride tetrahydrate as catalysts. Various products were quantitatively analyzed by liquid chromatography. The yields of lactic acids in the analytical results are shown in Table 7 below.

Example 45

Reaction was performed similarly to Example 37 except for using 32.7 mg (0.05 mmol) of rhenium carbonyl and further using 19.8 mg (0.1 mmol) of manganese chloride tetrahydrate as catalysts. Various products were quantitatively analyzed by liquid chromatography. The yields of lactic acids in the analytical results are shown in Table 7 below.

Example 46

Reaction was performed similarly to Example 37 except for using 0.45 g (2.5 mmol) of glucose instead of 0.45 g (2.5 mmol) of D-fructose as a raw material, using 32.7 mg (0.05 mmol) of rhenium carbonyl and 19.8 mg (0.1 mmol) of manganese chloride tetrahydrate as catalysts, and performing heat treatment at 160° C. for 24 hours of reaction time. Various products were quantitatively analyzed by liquid chromatography. The yields of lactic acids in the analytical results are shown in Table 7 below.

Example 47

Reaction was performed similarly to Example 37 except for using 0.428 g (1.25 mmol) of sucrose instead of 0.45 g (2.5 mmol) of D-fructose as a raw material, using 65.3 mg (0.1 mmol) of rhenium carbonyl and 19.8 mg (0.1 mmol) of manganese chloride tetrahydrate as catalysts, and performing heat treatment at 180° C. Various products were quantitatively analyzed by liquid chromatography. The yields of lactic acids in the analytical results are shown in Table 7 below.

Example 48

Reaction was performed similarly to Example 37 except for using 16.3 mg (0.025 mmol) of rhenium carbonyl and further using 16.1 mg (0.05 mmol) of magnesium trifluoromethanesulfonate as catalysts. Various products were quantitatively analyzed by liquid chromatography. The yields of lactic acids in the analytical results are shown in Table 7 below.

Example 49

Reaction was performed similarly to Example 37 except for using a combination of 19.8 mg (0.1 mmol) of manganese chloride tetrahydrate, 32.7 mg (0.05 mmol) of rhenium carbonyl, and 9.5 mg (0.05 mmol) of tin (II) chloride, as a catalyst. Various products were quantitatively analyzed by liquid chromatography. The yields of lactic acids in the analytical results are shown in Table 7 below.

(Results)

As shown in Table 7, lactic acid ester could be obtained in a high yield in the case (Example 37) of using rhenium carbonyl alone as a catalyst.

Furthermore, lactic acid ester could be obtained in a high yield in the cases of using rhenium carbonyl with a compound of a metal other than rhenium (Examples 38-43, 48, and 49). In particular, lactic acid ester could be obtained in an even higher yield in the combined use with magnesium chloride hexahydrate or manganese chloride tetrahydrate (Examples 38 and 39). Also, lactic acid ester could be obtained in particularly a high yield in the case of using rhenium carbonyl with two types of compound of a metal other than rhenium (Example 49). On the other hand, the production amount of lactic acid ester was low in the case (Comparative example 24) of using a compound of a metal other than rhenium alone as a catalyst.

In Examples 43 and 45 wherein the proportions of two types of catalyst were varied, the yield of lactic acid ester was higher in a case of a higher proportion (about 33%; Example 43) of rhenium carbonyl relative to the total amount of catalysts used than that in a case of a lower proportion (20%; Example 45) of the same. Therefore, it was demonstrated that when a compound of a metal other than rhenium is added to rhenium carbonyl, the relatively high proportion of rhenium carbonyl relative to the total amount of catalysts used is useful for obtaining lactic acid ester in a high yield.

Furthermore, lactic acid ester could be obtained in a high yield in the cases (Examples 46 and 47) of using rhenium carbonyl in combination with a compound of a metal other than rhenium and sugar other than fructose as a raw material.

TABLE 7

| | Raw material/ mmol | Catalyst/mmol | | | Temperature/ °C | Time/ h | Yield/% | | Recovery rate/% Saccharides |
|---|---|---|---|---|---|---|---|---|---|
| | | | | | | | Methyl lactate | Methyl levulinate | |
| Example 37 | Fructose/ 2.5 | $Re_2(CO)_{10}$/0.2 | | | 150 | 10 | 23 | 6 | 12 |
| Example 38 | Fructose/ 2.5 | $Re_2(CO)_{10}$/0.1 | $MgCl_2 \cdot 6H_2O$/ 0.1 | | 150 | 10 | 51 | 3 | 5 |
| Example 39 | Fructose/ 2.5 | $Re_2(CO)_{10}$/0.1 | $MnCl_2 \cdot 4H_2O$/ 0.1 | | 150 | 10 | 52 | trace | 6 |
| Example 40 | Fructose/ 2.5 | $Re_2(CO)_{10}$/0.1 | $FeCl_2 \cdot 6H_2O$/ 0.1 | | 150 | 10 | 44 | trace | 4 |
| Example 41 | Fructose/ 2.5 | $Re_2(CO)_{10}$/0.1 | $CoCl_2 \cdot 6H_2O$/ 0.1 | | 150 | 10 | 42 | trace | 5 |
| Example 42 | Fructose/ 2.5 | $Re_2(CO)_{10}$/0.1 | $NiCl_2 \cdot 4H_2O$/0.1 | | 150 | 10 | 38 | 1 | 8 |
| Example 43 | Fructose/ 2.5 | $Re_2(CO)_{10}$/0.1 | $SnCl_2$/0.1 | | 150 | 10 | 43 | 6 | 3 |
| Comparative example 24 | Fructose/ 2.5 | $MnCl_2 \cdot 4H_2O$/ 0.2 | | | 150 | 10 | 16 | trace | 40 |
| Example 44 | Fructose/ 2.5 | $Re_2(CO)_{10}$/0.025 | $MnCl_2 \cdot 4H_2O$/ 0.1 | | 150 | 10 | 38 | trace | 12 |
| Example 45 | Fructose/ 2.5 | $Re_2(CO)_{10}$/0.05 | $MnCl_2 \cdot 4H_2O$/ 0.1 | | 150 | 10 | 49 | trace | 10 |
| Example 46 | Glucose/ 2.5 | $Re_2(CO)_{10}$/0.05 | $MnCl_2 \cdot 4H_2O$/ 0.1 | | 160 | 24 | 44 | 1 | 4 |
| Example 47 | Sucrose/ 1.25 | $Re_2(CO)_{10}$/0.1 | $MnCl_2 \cdot 4H_2O$/ 0.1 | | 180 | 10 | 49 | 3 | 6 |
| Example 48 | Fructose/ 2.5 | $Re_2(CO)_{10}$/0.025 | $Mg(OTf)_2$/0.05 | | 150 | 10 | 30 | 6 | 15 |
| Example 49 | Fructose/ 2.5 | $Re_2(CO)_{10}$/ 0.05 | $MnCl_2 \cdot 4H_2O$/ 0.1 | $SnCl_2$/0.05 | 150 | 10 | 60 | 1 | 1 |

Tf = $CF_3SO_2$

Example 50

Cellulose (0.405 g) (corresponding to 2.5 mmol of glucose residue) that had been dried for 2 or more hours in air at 120° C., 31.9 mg (0.06 mmol) of di-n-butyltin (II) trifluoromethanesulfonate, 9.9 mg (0.05 mmol) of manganese chloride tetrahydrate, 16.3 mg (0.025 mmol) of rhenium carbonyl, 20 mL of methanol, and a stirring bar were added to a 50-mL stainless-steel autoclave, and then the lid was closed. Air in the autoclave was purged with nitrogen gas. After pressurization to 0.5 MPa, the interior of the autoclave was heated to 200° C. using a mantle heater while stirring the mixture with a magnetic stirrer. Subsequently, stirring was continued for 24 hours while maintaining a temperature of 200° C., heating was then stopped, and then the autoclave was left to cool at room temperature. The reaction solution was removed from the autoclave after cooling to room temperature, and various products in the solution were quantitatively analyzed by liquid chromatography. The yields of lactic acids in the analytical results are shown in Table 8 below. In Table 8, "-" indicates that the percentage is equal to or less than the detection limit.

Example 51

63.7 mg (0.12 mmol) of di-n-butyltin (II) trifluoromethanesulfonate, 19.8 mg (0.1 mmol) of manganese chloride tetrahydrate, and 32.6 mg (0.05 mmol) of rhenium carbonyl were used as catalysts. Reaction was performed under conditions similar to those of Example 50 except for the above conditions. Various products in the thus obtained reaction solution were quantitatively analyzed by liquid chromatography. The yields of lactic acids in the analytical results are shown in Table 8 below.

Example 52

Heat treatment was performed for 62 hours of reaction time using 31.9 mg (0.06 mmol) of di-n-butyltin (II) trifluoromethanesulfonate, 10.2 mg (0.05 mmol) of magnesium chloride hexahydrate, and 16.3 mg (0.025 mmol) of rhenium carbonyl, as catalysts. Reaction was performed under conditions similar to those of Example 50 except for the above conditions. Various products in the thus obtained reaction solution were quantitatively analyzed by liquid chromatography. The yields of lactic acids in the analytical results are shown in Table 8 below.

Example 53

Heat treatment was performed for 10 hours of reaction time using 50.0 mg (0.12 mmol) of tin (II) trifluoromethanesulfonate, 19.8 mg (0.1 mmol) of manganese chloride tetrahydrate, and 32.6 mg (0.05 mmol) of rhenium carbonyl ($Re_2(CO)_{10}$) as catalysts. Reaction was performed under conditions similar to those of Example 50 except for the above conditions. Various products in the thus obtained reaction solution were quantitatively analyzed by liquid chromatography. The yields of lactic acids in the analytical results are shown in Table 8 below.

Comparative Example 25

Di-n-butyltin (II) trifluoromethanesulfonate (63.7 mg (0.12 mmol)) and 19.8 mg (0.1 mmol) of manganese chloride tetrahydrate were used as catalysts. Reaction was performed under conditions similar to those of Example 50 except for the above conditions. Various products in the thus obtained reaction solution were quantitatively analyzed by liquid chromatography. The yields of lactic acids in the analytical results are shown in Table 8 below.

Comparative Example 26

Heat treatment was performed at 190° C. for 10 hours of reaction time using 10.6 mg (0.02 mmol) of di-n-butyltin (II) trifluoromethanesulfonate alone as a catalyst. Reaction was performed under conditions similar to those of Example 50 except for the above conditions. Various products in the thus obtained reaction solution were quantitatively analyzed by liquid chromatography. The yields of lactic acids in the analytical results are shown in Table 8 below.

Comparative Example 27

Heat treatment was performed at 190° C. for 10 hours of reaction time using 8.3 mg (0.02 mmol) of tin (II) trifluoromethanesulfonate alone as a catalyst. Reaction was performed under conditions similar to those of Example 50 except for the above conditions. Various products in the thus obtained reaction solution were quantitatively analyzed by liquid chromatography. The yields of lactic acids in the analytical results are shown in Table 8 below.

Comparative Example 28

Heat treatment was performed at 190° C. for 10 hours of reaction time using 53.1 mg (0.1 mmol) of di-n-butyltin (II) trifluoromethanesulfonate alone as a catalyst. Reaction was performed under conditions similar to those of Example 50 except for the above conditions. Various products in the thus obtained reaction solution were quantitatively analyzed by liquid chromatography. The yields of lactic acids in the analytical results are shown in Table 8 below.

Comparative Example 29

Heat treatment was performed at 190° C. for 10 hours of reaction time using 41.6 mg (0.1 mmol) of tin (II) trifluoromethanesulfonate alone as a catalyst. Reaction was performed under conditions similar to those of Example 50 except for the above conditions. Various products in the thus obtained reaction solution were quantitatively analyzed by liquid chromatography. The yields of lactic acids in the analytical results are shown in Table 8 below.

(Results)

As shown in Table 8, in the presence of tin or organic tin trifluoromethanesulfonate, lactic acid ester could be obtained (using cellulose as a raw material) in a high yield in the cases (Examples 50-53) of using rhenium carbonyl in combination with a magnesium compound or a manganese compound as a catalyst, compared with the cases (Comparative examples 25-29) of not using a combination of the three types of catalyst. Furthermore, regarding Examples 50 and 51 in which the ratio of the amounts of the three types of catalyst was varied, lactic acid ester was obtained in a yield higher in the case of the lower total amount of the catalysts used than in the case of the higher total amount of the same. Therefore, it was demonstrated that when three types of catalyst were added, the relatively low total amount of catalysts used is useful for obtaining lactic acid ester in a high yield. In addition, lactic acid ester was generated but no lactic acid was generated in the case of using rhenium carbonyl or a manganese compound.

TABLE 8

| | Catalyst/mmol | | | Temperature/ °C. | Time/ h | Yield/% | | | |
|---|---|---|---|---|---|---|---|---|---|
| | | | | | | Methyl lactate | Lactic acid | Total (Lactic acids) | Methyl levulinate |
| Example 50 | Re$_2$(CO)$_{10}$/0.025 | MnCl$_2$•4H$_2$O/0.05 | "Bu$_2$Sn(OTf)$_2$/0.06 | 200 | 24 | 46 | — | 46 | 3 |
| Example 51 | Re$_2$(CO)$_{10}$/0.05 | MnCl$_2$•4H$_2$O/0.1 | "Bu$_2$Sn(OTf)$_2$/0.12 | 200 | 24 | 42 | — | 42 | 7 |
| Example 52 | Re$_2$(CO)$_{10}$/0.025 | MgCl$_2$•6H$_2$O/0.05 | "Bu$_2$Sn(OTf)$_2$/0.06 | 200 | 62 | 44 | — | 44 | 4 |
| Example 53 | Re$_2$(CO)$_{10}$/0.05 | MnCl$_2$•4H$_2$O/0.1 | Sn(OTf)$_2$/0.12 | 200 | 10 | 39 | — | 39 | 10 |
| Comparative example 25 | | MnCl$_2$•4H$_2$O/0.1 | "Bu$_2$Sn(OTf)$_2$/0.12 | 200 | 24 | 32 | — | 32 | 10 |
| Comparative example 26 | | | "Bu$_2$Sn(OTf)$_2$/0.02 | 190 | 10 | 29 | 6 | 35 | 22 |
| Comparative example 27 | | | Sn(OTf)$_2$/0.02 | 190 | 10 | 14 | 12 | 26 | 22 |
| Comparative example 28 | | | "Bu$_2$Sn(OTf)$_2$/0.1 | 190 | 10 | 23 | 2 | 25 | 20 |
| Comparative example 29 | | | Sn(OTf)$_2$/0.1 | 190 | 10 | 20 | 4 | 24 | 24 |

Tf = CF$_3$SO$_2$

Example 54

Generation of Ate Complex of Rhenium

Manganese chloride tetrahydrate (9.9 mg (0.05 mmol)), 16.3 mg (0.025 mmol) of rhenium carbonyl, and 10 mL of methanol were added to a high-pressure reaction vessel and then the vessel was sealed, followed by pressurization with nitrogen to 0.5 MPa. Subsequently, the temperature of the reaction vessel was increased from room temperature to 150° C. for 45 minutes in an electric furnace, the reaction vessel was immediately cooled, and then ESI/MS measurement was performed for the content.

Based on the measurement results, the generation of the ate complex of rhenium was observed (FIG. 1).

Therefore, it was suggested that rhenium carbonyl formed an ate complex with a compound of a metal other than rhenium, and that the complex acted as a catalyst for a degradation reaction of cellulose, as well as sugar degradation•isomerization reaction.

(3) Method Using Indium Alkoxide and the Like as Catalysts

Example 55

Lactic Acid Ester Synthesis from Fructose Using an Indium Compound

Indium isopropoxide (15 mg (0.05 mmol)) as an indium compound, 0.450 g (2.5 mmol) of fructose as carbohydrate (as a raw material), and 10 mL of methanol as a solvent were added to a stainless-steel compression reactor (Nitto Koatsu Co. Ltd.) with an inner volume of 50 ml at room temperature. Then nitrogen gas (0.5 MPa) was injected into the reactor vessel of the reactor, and then the inside of the reactor vessel was heated to 150° C. using a mantle heater. After the temperature was maintained at 150° C. for 10 hours, heating was stopped, and then the reactor was left to cool. After the reactor was cooled to room temperature, the remaining organic phase was removed by pressure discharge, and then the thus obtained solution was quantitatively analyzed by liquid chromatography. As a result, 2.4 mmol of methyl lactate was generated. The yield of the methyl lactate was 48% when represented in percentage (%) figures for the number of moles of methyl lactate generated per mole of fructose as a raw material (fructose standard).

Example 56

Lactic Acid Synthesis from Fructose Using Indium Compound

Indium isopropoxide (15 mg (0.05 mmol)) as an indium compound, 0.450 g (2.5 mmol) of fructose as carbohydrate (as a raw material), and 10 mL of pure water as a solvent were added to a stainless-steel compression reactor (Nitto Koatsu Co. Ltd.) with an inner volume of 50 mL at room temperature. Nitrogen gas (0.5 MPa) was injected into the reactor vessel of the reactor and then the interior of the reactor vessel was heated to 160° C. using a mantle heater. The temperature was maintained at 160° C. for 5 hours, heating was stopped, and then the reactor was left to cool. The remaining organic phase was removed by pressure discharge after cooling of the reactor to room temperature, and then the thus obtained solution was quantitatively analyzed by liquid chromatography. As a result, 0.24 mmol of lactic acid was generated. The yield of lactic acid was 5% when it is represented by the fructose standard; that is, in percentage (%) figures for the number of moles (mol) of lactic acid (per mol of fructose as a raw material).

Example 57

Lactic Acid Ester Synthesis from Glucose Using Indium Compound

Reaction was performed under the same conditions as those in Example 55 except for using 0.450 g (2.5 mmol) of glucose instead of fructose as carbohydrate (as a raw material) and a reaction temperature of 180° C. As a result, 2.0 mmol (yield of 40% based on the glucose standard) of methyl lactate was generated and 0.08 mmol (yield of 3% based on the glucose standard) of methyl levulinate was generated as a by-product. The term "glucose standard" refers to the percentage (%) figure representing the number of moles of a product generated per mole of glucose as a raw material.

Example 58

Lactic Acid Ester Synthesis from Glucose Using Indium Acetylacetonate

Reaction was performed under the same conditions as those in Example 55 except for using 20.8 mg (0.05 mmol) of indium acetylacetone (In(acac)$_3$) as an indium compound. As a result, 1.55 mmol (yield of 31% based on the fructose standard) of methyl lactate was generated, but no methyl levulinate was generated.

Example 59

Effects of the Addition of a Phenolic Compound

Reaction was performed under the same conditions as those in Example 55 except for adding, in addition to indium isopropoxide, fructose, and methanol, 0.1 mmol of catechol as a phenolic compound to a reactor vessel. As a result, 2.6 mmol (yield of 52% based on the fructose standard) of methyl lactate was generated and 0.15 mmol (yield of 6% based on the glucose standard) of methyl levulinate was generated as a by-product.

Example 60

Effects of the Addition of Phenolic Compound

Reaction was performed under the same conditions as those in Example 55 except for adding, in addition to indium isopropoxide, fructose, and methanol, 0.1 mmol of 2,2-biphenol as a phenolic compound to a reaction vessel. As a result, 2.5 mmol (yield of 50% based on the fructose standard) of methyl lactate was generated.

(4) Method Using Indium Compound and the Like as Catalysts

Example 61

Indium (III) chloride tetrahydrate (14.9 mg (0.05 mmol)) as a metal compound, 28.7 mg (0.05 mmol) of bis(triphenylphosphine)iminium chloride as a salt, 0.45 g (2.5 mmol) of fructose as carbohydrate (as a raw material), 20 mL of methanol as a solvent, and a stirring bar were added to a stainless-steel compression reactor with an inner volume of 50 mL (Nitto Koatsu Co. Ltd.), and then the lid was closed. Air in the autoclave was purged with nitrogen gas. After pressurization to 0.5 MPa, the autoclave was heated to 150° C. using an electric furnace while stirring the mixture with a magnetic stirrer. Subsequently, stirring was continued for 5 hours while maintaining a temperature of 150° C., and then the autoclave was left to cool at room temperature. The reaction solution was removed from the autoclave after cooling, and products in the solution were quantitatively analyzed by liquid chromatography. The yields of lactic acids in the analytical results are shown in Table 9 below. Each yield is represented in percentage (%) figures for the number of moles (mol) of each product with respect to the number of moles (lactic acids/fructose=5 mmol/2.5 mmol) of lactic acids theoretically generated from D-fructose as a raw material.

Example 62

Reaction was performed similarly to Example 61 except for performing heat treatment at 180° C. Products in the solution were quantitatively analyzed by liquid chromatography. The yields of lactic acids in the analytical results are shown in Table 9 below.

Example 63

Reaction was performed similarly to Example 62 except for using 17.7 mg (0.05 mmol) of indium bromide (III) as a metal compound. Products in the solution were quantitatively analyzed by liquid chromatography. The yields of lactic acids in the analytical results are shown in Table 9 below.

Example 64

Reaction was performed similarly to Example 62 except for using 14.6 mg (0.05 mmol) of indium (III) acetate as a metal compound. Products in the solution were quantitatively analyzed by liquid chromatography. The yields of lactic acids in the analytical results are shown in Table 9 below.

Example 65

Reaction was performed similarly to Example 62 except for using 20.6 mg (0.05 mmol) of indium (III) acetylacetone as a metal compound. Products in the solution were quantitatively analyzed by liquid chromatography. The yields of lactic acids in the analytical results are shown in Table 9 below.

Example 66

Reaction was performed similarly to Example 62 except for using 30.9 mg (0.05 mmol) of bis(triphenylphosphine) iminium bromide as a salt. Products in the solution were quantitatively analyzed by liquid chromatography. The yields of lactic acids in the analytical results are shown in Table 9 below.

Example 67

Reaction was performed similarly to Example 62 except for using 33.3 mg (0.05 mmol) of bis(triphenylphosphine) iminium iodine as a salt. Products in the solution were quantitatively analyzed by liquid chromatography. The yields of lactic acids in the analytical results are shown in Table 9 below.

Example 68

Reaction was performed similarly to Example 62 except for using 2.1 mg (0.05 mmol) of lithium chloride as a salt. Products in the solution were quantitatively analyzed by liquid chromatography. The yields of lactic acids in the analytical results are shown in Table 9 below.

Example 69

Reaction was performed similarly to Example 62 except for using 9.9 mg (0.05 mmol) of 1-butyl-3-methylimidazoliumacetate as a salt. Products in the solution were quantitatively analyzed by liquid chromatography. The yields of lactic acids in the analytical results are shown in Table 9 below.

Example 70

Reaction was performed similarly to Example 62 except for using 11.3 mg (0.05 mmol) of 1-butyl-3-methylimidazoliumtetrafluoroborate as a salt. Products in the solution were quantitatively analyzed by liquid chromatography. The yields of lactic acids in the analytical results are shown in Table 9 below.

Example 71

Reaction was performed similarly to Example 62 except for using 7.3 mg (0.05 mmol) of sodium picolinate as a salt. Products in the solution were quantitatively analyzed by liquid chromatography. The yields of lactic acids in the analytical results are shown in Table 9 below.

Example 72

Reaction was performed similarly to Example 62 except for using 8.1 mg (0.05 mmol) of sodium(trihydroxy)phenylborate as a salt. Products in the solution were quantitatively analyzed by liquid chromatography. The yields of lactic acids in the analytical results are shown in Table 9 below.

Example 73

Reaction was performed similarly to Example 61 except for using 8.8 mg (0.05 mmol) of gallium (III) trichloride as a metal compound, performing heat treatment at 190° C., and stirring for 2 hours. Products in the solution were quantitatively analyzed by liquid chromatography. The yields of lactic acids in the analytical results are shown in Table 9 below.

Example 74

Reaction was performed similarly to Example 61 except for using 12.1 mg (0.05 mmol) of aluminium (III) chloride hexahydrate as a metal compound, performing heat treatment at 190° C., and stirring for 2 hours. Products in the solution were quantitatively analyzed by liquid chromatography. The yields of lactic acids in the analytical results are shown in Table 9 below.

(Results)

As shown in Table 9, as a result of using the ate complex generated by reaction of a metal compound with a salt as a catalyst, lactic acids could be obtained in high yields. In particular, lactic acids were obtained in high yields of more than 60% in the cases (Examples 62, 63, 66, 67, 68, 69, 71, and 72) of using indium (III) chloride tetrahydrate as a metal compound and bis(triphenylphosphine)iminium salt, lithium chloride, 1-butyl-3-methylimidazoliumacetate, sodium picolinate, or sodium(trihydroxy)phenylborate as a salt, and performing heat treatment at 180° C.

TABLE 9

| Example | Metal compound | Salt | Temperature (° C.) | Time (h) | Yield (%) |
|---|---|---|---|---|---|
| 61 | $InCl_3 \cdot 4H_2O$ | [PPN]Cl | 150 | 5 | 51.1% |
| 62 | $InCl_3 \cdot 4H_2O$ | [PPN]Cl | 180 | 5 | 62.8% |
| 63 | $InBr_3$ | [PPN]Cl | 180 | 5 | 60.9% |
| 64 | $In(OAc)_3$ | [PPN]Cl | 180 | 5 | 51.0% |
| 65 | $In(acac)_3$ | [PPN]Cl | 180 | 5 | 26.7% |
| 66 | $InCl_3 \cdot 4H_2O$ | [PPN]Br | 180 | 5 | 62.5% |
| 67 | $InCl_3 \cdot 4H_2O$ | [PPN]I | 180 | 5 | 63.0% |
| 68 | $InCl_3 \cdot 4H_2O$ | LiCl | 180 | 5 | 61.0% |
| 69 | $InCl_3 \cdot 4H_2O$ | [bmim]OAc | 180 | 5 | 61.4% |
| 70 | $InCl_3 \cdot 4H_2O$ | [bmim]$BF_4$ | 180 | 5 | 58.6% |
| 71 | $InCl_3 \cdot 4H_2O$ | Sodium picolinate | 180 | 5 | 65.0% |
| 72 | $InCl_3 \cdot 4H_2O$ | Sodium(trihydroxy)phenylborate | 180 | 5 | 63.3% |
| 73 | $GaCl_3$ | [PPN]Cl | 190 | 2 | 33.9% |
| 74 | $AlCl_3 \cdot 6H_2O$ | [PPN]Cl | 190 | 2 | 20.9% |

Example 75

Generation of Ate Complex

Indium (III) chloride tetrahydrate (0.05 mmol) as a metal compound and bis(triphenylphosphine)iminium chloride (0.05 mmol) as a salt were dissolved in methanol (20 mL), and then the solution was heated in an autoclave under nitrogen gas (0.5 MPa) at 190° C. for 2 hours (no sugar (carbohydrate as a raw material) was added, but treatment was performed under the same reaction conditions as those in Example 61). Subsequently, the autoclave was left to cool at room temperature. After cooling, the reaction solution was removed from the autoclave and then products in the solution were measured by ESI-MS.

Figure 2:
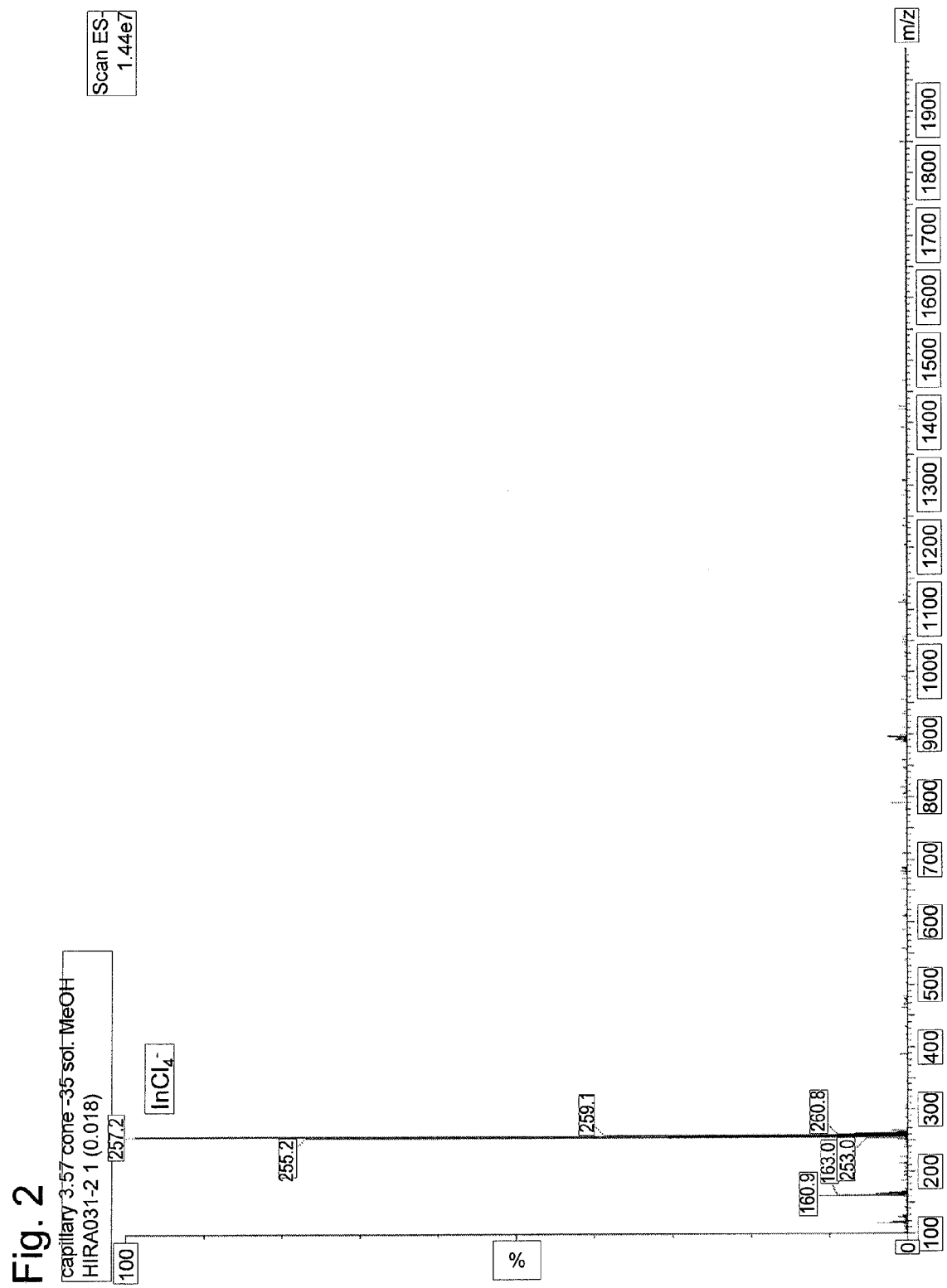
FIG. 2 shows the results of ESI/MS measurement for ate complexes generated by indium chloride (III) tetrahydrate and bis(triphenylphosphine)iminium chloride.

As a result of measurement, the generation of the ate complex of $InCl_4^-$ was observed (FIG. 2).

Therefore, it was suggested that indium (III) chloride tetrahydrate and bis(triphenylphosphine)iminium chloride form an ate complex and the complex acts as a catalyst for sugar degradation•isomerization reaction.

Example 76

Indium (III) chloride tetrahydrate (14.9 mg (0.05 mmol)) and 31.9 mg (0.06 mmol) of dibutyltin triflate as metal compounds, 28.7 mg (0.05 mmol) of bis(triphenylphosphine)iminium chloride as a salt, 0.405 g of cellulose (corresponding to 2.5 mmol in terms of glucose unit) as carbohydrate (as a raw material), 20 mL of methanol as a solvent, and a stirring bar were added to a stainless-steel compression reactor with an inner volume of 190 mL (Tokyo Rikakikai Co., Ltd.), and then the lid was closed. Air in the autoclave was purged with nitrogen gas. After pressurization to 0.5 MPa, the autoclave was heated to 190° C. using an electric furnace while stirring the mixture with a magnetic stirrer. Subsequently, stirring was continued for 10 hours while maintaining a temperature of 190° C., and then the autoclave was left to cool at room temperature. The reaction solution was removed from the autoclave after cooling, and products in the solution were quantitatively analyzed by liquid chromatography. The yields of lactic acids in the analytical results are shown in Table 10 below. Each yield is represented in percentage (%) figures for the number of moles (mol) of each product with respect to the number of moles (lactic acids/glucose unit in cellulose=5 mmol/2.5 mmol) of lactic acids theoretically generated from cellulose as a raw material.

Example 77

Reaction was performed similarly to Example 76 except for using 14.9 mg (0.05 mmol) of indium (III) chloride tetrahydrate and 25.0 mg (0.06 mmol) of tin triflate as metal compounds. Products in the solution were quantitatively analyzed by liquid chromatography. The yields of lactic acids in the analytical results are shown in Table 10 below.

TABLE 10

| Example | Metal compound | Salt | Temperature (° C.) | Time (h) | Yield (%) |
|---|---|---|---|---|---|
| 76 | Bu$_2$Sn(OTf)$_2$ InCl$_3$ 4H$_2$O | [PPN]Cl | 190 | 10 | 32.6% |
| 77 | Sn(OTf)$_2$ InCl$_3$ 4H$_2$O | [PPN]Cl | 190 | 10 | 28.7% |

Comparative Example 30

Reaction was performed similarly to Example 76 except for using 31.9 mg (0.06 mmol) of dibutyltin triflate alone as a metal compound without adding a salt. Products in the solution were quantitatively analyzed by liquid chromatography. The yields of lactic acids in the analytical results are shown in Table 11 below.

Comparative Example 31

Reaction was performed similarly to Comparative example 30 except for using 25.0 mg (0.06 mmol) of tin triflate as a metal compound. Products in the solution were quantitatively analyzed by liquid chromatography. The yields of lactic acids in the analytical results are shown in Table 11 below.

Comparative Example 32

Reaction was performed similarly to Comparative example 30 except for using 14.9 mg (0.05 mmol) of indium (III) chloride tetrahydrate as a metal compound and 28.7 mg (0.05 mmol) of bis(triphenylphosphine)iminium chloride as a salt. Products in the solution were quantitatively analyzed by liquid chromatography. The yields of lactic acids in the analytical results are shown in Table 11 below.

TABLE 11

| Comparative example | Metal compound | Salt | Temperature (° C.) | Time (h) | Yield (%) |
|---|---|---|---|---|---|
| 30 | Bu$_2$Sn(OTf)$_2$ | — | 190 | 10 | 16.0% |
| 31 | Sn(OTf)$_2$ | — | 190 | 10 | 18.0% |
| 32 | InCl$_3$ 4H$_2$O | [PPN]Cl | 190 | 10 | — |

Based on the results of Examples 76 and 77 and Comparative examples 30-32, it was revealed that the use of a tin compound with a combination of an indium compound and a salt results in an improved lactic acid yield from cellulose.

INDUSTRIAL APPLICABILITY

The method of the present invention provides a novel catalytic reaction system for efficiently converting biomass containing polysaccharides represented by cellulose and monosaccharides into lactic acid and lactic acid ester. The use of the method of the present invention enables efficient production of lactic acid and/or lactic acid ester using a carbohydrate-containing raw material, such as biomass containing a cellulose resource. According to the method, lactic acid and/or lactic acid ester, and particularly lactic acid ester can be produced in a high yield without using a large amount of strong acid, while suppressing the generation of by-products.

All publications, patents and patent applications cited in this description are herein incorporated by reference in their entirety.

The invention claimed is:

1. A method for producing lactic acid, lactic acid ester, or both lactic acid and lactic acid ester comprising heating a carbohydrate-containing raw material in a solvent containing a catalyst, wherein the catalyst is a tin perfluoroalkylsulfonate compound or an organic tin perfluoroalkylsulfonate compound, and wherein the solvent comprises water, alcohol, or a combination of water and alcohol.

2. The method according to claim 1, wherein the catalyst further comprises at least one compound selected from the group consisting of a tin compound, an indium compound and a rhenium compound.

3. The method according to claim 1, wherein the solvent further comprises at least one compound selected from the group consisting of a first transition metals series compound, a lithium compound, a magnesium compound, an alkali metal salt, an alkaline earth metal salt, a quaternary ammonium salt, and a quaternary phosphonium salt.

4. The method according to claim 2, wherein the solvent further comprises at least one additional compound selected from the group consisting of a first transition metals series compound, a lithium compound, a magnesium compound, an alkali metal salt, an alkaline earth metal salt, a quaternary ammonium salt, and a quaternary phosphonium salt, and wherein the at least one additional compound forms an ate complex with the at least one compound selected from the group consisting of a tin compound, and indium compound, and an rhenium compound.

5. The method according to claim 2, wherein the indium compound is selected from the group consisting of a halide salt, carboxylate, indium alkoxide, and indium acetylacetate.

6. The method according to claim 2, wherein the rhenium compound is a compound containing a halide or a carbonyl ligand.

7. The method according to claim 1, wherein the solvent further comprises a phenolic compound.

8. The method according to claim 1, wherein heating is performed at 100° C. to 300° C.

9. The method according to claim 1, wherein the carbohydrate-containing raw material is at least one material selected from the group consisting of cellulose, soluble polysaccharides, and monosaccharides.

* * * * *